(12) United States Patent
Hu et al.

(10) Patent No.: US 10,551,523 B2
(45) Date of Patent: Feb. 4, 2020

(54) EVALUATING AND IMAGING VOLUMETRIC VOID SPACE LOCATION FOR CEMENT EVALUATION

(71) Applicant: Halliburton Energy Services, Inc., Houston, TX (US)

(72) Inventors: Yike Hu, Houston, TX (US); Weijun Guo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 79 days.

(21) Appl. No.: 15/320,908

(22) PCT Filed: Aug. 19, 2015

(86) PCT No.: PCT/US2015/045905
§ 371 (c)(1),
(2) Date: Dec. 21, 2016

(87) PCT Pub. No.: WO2017/030579
PCT Pub. Date: Feb. 23, 2017

(65) Prior Publication Data
US 2017/0199298 A1    Jul. 13, 2017

(51) Int. Cl.
*G01V 5/12*    (2006.01)
*E21B 47/00*    (2012.01)
(Continued)

(52) U.S. Cl.
CPC .............. *G01V 5/12* (2013.01); *E21B 33/14* (2013.01); *E21B 47/0005* (2013.01); *E21B 47/082* (2013.01); *G01N 33/383* (2013.01)

(58) Field of Classification Search
CPC ....... G01V 5/12; E21B 33/14; E21B 47/0005; E21B 47/082; G01N 33/383
See application file for complete search history.

(56) References Cited

U.S. PATENT DOCUMENTS

| 2,451,472 A | * | 10/1948 | Coggeshall | ......... E21B 47/0005 166/253.1 |
| 3,081,401 A | | 3/1963 | Wilson | |

(Continued)

FOREIGN PATENT DOCUMENTS

| EP | 816872 A1 | 1/1998 |
| EP | 2309259 A1 | 4/2011 |

(Continued)

OTHER PUBLICATIONS

Yuan et al., "HPHT Gas Well Cementing Complications and Its Effect on Casing Collapse Resistance," SPE 153986 (2012).
(Continued)

*Primary Examiner* — David P Porta
*Assistant Examiner* — Jeremy S Valentiner
(74) *Attorney, Agent, or Firm* — Benjamin Fite; C. Tumey Law Group PLLC

(57) ABSTRACT

Methods including taking a gamma spectrum from a wellbore at a target depth, wherein the wellbore penetrates a subterranean formation and has a completion profile comprising a pipe and an annulus between the pipe and the subterranean formation; determining a cement volumetric void space in the wellbore at the target depth; establishing a cement-void-spatial calibration curve based on obtained gamma spectra representing cement spatial void space locations in the annulus of the completion profile, wherein each cement volumetric void space amount in the wellbore has a characteristic cement-void-spatial calibration curve; comparing the wellbore gamma spectrum and the cement-void-spatial calibration curve; and determining a location of the cement volumetric void space in the wellbore at the target depth.

20 Claims, 14 Drawing Sheets

(51) Int. Cl.
*E21B 33/14* (2006.01)
*E21B 47/08* (2012.01)
*G01N 33/38* (2006.01)

(56) References Cited

U.S. PATENT DOCUMENTS

| | | | |
|---|---|---|---|
| 3,110,807 A | 11/1963 | Wilson | |
| 3,521,065 A * | 7/1970 | Locke | G01V 5/145 |
| | | | 250/264 |
| 3,848,124 A * | 11/1974 | Vann | E21B 47/0005 |
| | | | 250/260 |
| 5,001,342 A * | 3/1991 | Rambow | E21B 47/0005 |
| | | | 250/259 |
| 5,578,820 A * | 11/1996 | Gadeken | G01V 5/06 |
| | | | 250/256 |
| 7,289,916 B2 | 10/2007 | Drnevich et al. | |
| 7,639,563 B2 | 12/2009 | Wu et al. | |
| 8,950,482 B2 | 2/2015 | Hill et al. | |
| 2005/0128873 A1 | 6/2005 | LaBry | |
| 2006/0133203 A1 | 6/2006 | James | |
| 2006/0133204 A1 | 6/2006 | Froelich | |
| 2007/0263212 A1 | 11/2007 | Mound | |
| 2008/0116365 A1 | 5/2008 | Flecker | |
| 2010/0126718 A1 | 5/2010 | Lilley | |
| 2012/0033528 A1 | 2/2012 | Zhao et al. | |
| 2012/0158333 A1 | 6/2012 | Li et al. | |
| 2012/0327410 A1 | 12/2012 | Maston | |
| 2013/0261974 A1 * | 10/2013 | Stewart | G01V 5/125 |
| | | | 702/8 |
| 2013/0345983 A1 * | 12/2013 | Guo | G01V 5/104 |
| | | | 702/8 |
| 2014/0052376 A1 | 2/2014 | Guo et al. | |
| 2014/0374582 A1 * | 12/2014 | Guo | G01V 5/125 |
| | | | 250/269.3 |
| 2015/0090871 A1 * | 4/2015 | Chace | E21B 47/0005 |
| | | | 250/269.7 |
| 2016/0326865 A1 * | 11/2016 | Zhang | E21B 47/0005 |

FOREIGN PATENT DOCUMENTS

| | | |
|---|---|---|
| WO | 2010054387 A2 | 5/2010 |
| WO | 2013156843 A1 | 10/2013 |

OTHER PUBLICATIONS

Xu et al., "An Experimental Study of the Nano-Scratch Behavior of Cement Composite Material," Key Engineering Materials, vol. 492, pp. 47-54, Sep. 2011.

ISR/WO for PCT/US2015/045905 dated May 19, 2016.

* cited by examiner

EVALUATING AND IMAGING VOLUMETRIC VOID SPACE LOCATION FOR CEMENT EVALUATION

BACKGROUND

The present disclosure relates to subterranean formation operations and, more particularly, to determining a volumetric void space location for a particular volumetric void space amount in wellbore cement columns.

Subterranean formation operations (e.g., stimulation operations, sand control operations, completion operations, etc.) often involve drilling a wellbore in a subterranean formation with a drilling fluid (and thereafter placing a cement column between the formation and a casing (or liner string) in the wellbore. The cement column is formed by pumping a cement slurry through the bottom of the casing and out through an annulus between the outer casing wall and the formation face of the wellbore, or by directly pumping a cement slurry into the annulus. The cement slurry then cures in the annular space, thereby forming a column of hardened cement that, inter alia, supports and positions the casing in the wellbore and bonds the exterior surface of the casing to the subterranean formation. This process is referred to as "primary cementing."

Among other things, the cement column may keep fresh water reservoirs from becoming contaminated with produced fluids from within the wellbore. As used herein, the term "fluid" refers to liquid phase fluids and gas phase fluids. The cement column may also prevent unstable formations from caving in, thereby reducing the chance of a casing collapse and/or stuck drill pipe. Finally, the cement column forms a solid barrier to prevent fluid loss or contamination of production zones. The degree of success of a subterranean formation operation involving placement of a cement column, therefore, depends, at least in part, upon the successful cementing of the wellbore casing and the cement's ability to maintain zonal isolation of the wellbore.

Failure of zonal isolation, among other things, may result in environmental contamination, which may cause harm to both flora and fauna, including humans. Such failure may further prevent production or reduce the production capability of a wellbore, which may result in abandonment. These issues may become exacerbated over time, where an understanding of the state of the cement column at an earlier point in time may allow remedial actions to be performed and abandonment avoided. Furthermore, the location of a cement volumetric void space within the cement column may enable corrective measures to prevent failure of zonal isolation.

BRIEF DESCRIPTION OF THE DRAWINGS

The following figure is included to illustrate certain aspects of the embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
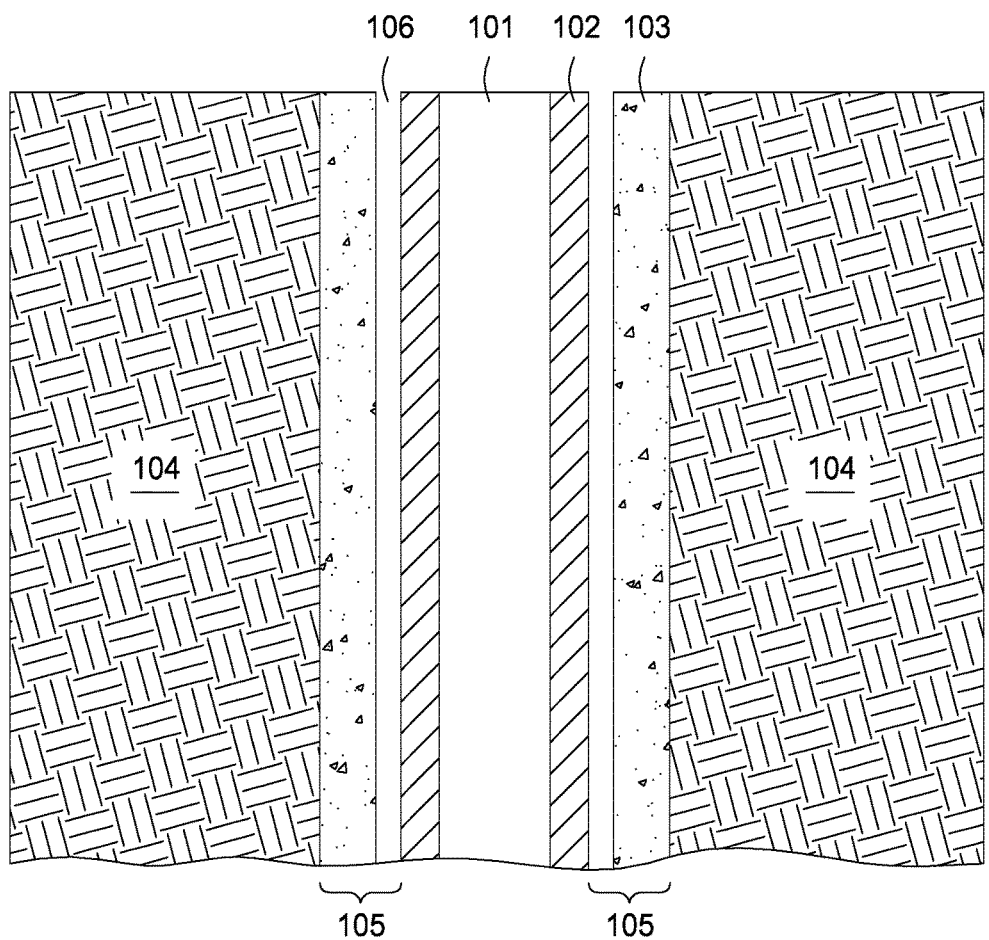
FIG. 1 is a cross-sectional diagram of a cased wellbore in a subterranean formation, according to one or more embodiments of the present disclosure.

The present disclosure relates to subterranean formation operations and, more particularly, to determining a volumetric void space location for a particular volumetric void space amount in wellbore cement columns. The determination may rely on a heterogeneity profiling analysis for first determining volumetric void space amount in a wellbore cement column. For example, the embodiments of the present disclosure may rely on first determining a heterogeneity profiling factor ("HPF") representing a specific volumetric void space amount for a particular wellbore having a cement column therein, and thereafter establishing the location of the particular volumetric void space amount within the cement column. As used herein, the term "heterogeneity profiling factor" or "HPF," and grammatical variants thereof, refers to a comparison between two gamma spectra (e.g., depicting a shape change therebetween or establishing a correlation coefficient therebetween).

The term "wellbore heterogeneity profiling factor" or "wellbore HPF," and grammatical variants thereof, refers to a comparison between a gamma spectrum of a cement column within a wellbore and a standard gamma spectrum, wherein the standard gamma spectrum is taken from a free-pipe and/or well-bonded standard having the same completion profile as the wellbore. As used herein, the term "free-pipe" refers to a cement column having no cement (0%) therein and the term "well-bonded" refers to a cement column having cement therein that fully fills the annulus, as described above. The term "completion profile," as used herein, refers to the size and shape of the wellbore, pipe (i.e., pipe forming the annulus between itself and the wellbore wall, such as casing string), and annulus, regardless of whether the wellbore is actual or simulated (e.g., via electronic means or laboratory means). The wellbore HPF, whether using the free-pipe or well-bonded standard, or both, can then be compared to a cement quality curve representing a volumetric void space of the completion profile. Accordingly, the volumetric void space in the cement column in the wellbore can be determined. Such volumetric void space can be established at one or more target depths within the wellbore. As used herein, the term "target depth" or simply "depth" with reference to a wellbore refers to the length of the wellbore, not necessarily a vertical depth from a surface location, as wellbores for use in the embodiments herein may be vertical, horizontal, deviated (i.e., neither vertical nor horizontal), or combinations thereof.

Once the volumetric void space in a particular wellbore having a particular completion profile is determined or otherwise known (e.g., a void space of 10%, or 20%, and the like), a cement-void-spatial calibration curve may be applied to determine the location of the volumetric void space within the cement column. As used herein, the term "cement-void-spatial calibration curve" refers to a graphical curve based on obtained gamma spectra representing cement spatial void locations for a particular volumetric void space amount within a cement column and for a particular completion profile. Accordingly, a separate cement-void-spatial calibration curve is established for each volumetric void space amount for each completion profile. For example, completion profile A will have a cement-void-spatial calibration curve for, for instance, 5% volumetric void space, 10% volumetric void space, 50% volumetric void space, and the like (this is a non-limiting example), wherein each curve identifies the location of the volumetric void space amount within the cement column, as described in greater detail below. A wellbore gamma spectrum taken of an actual wellbore with a known volumetric void space is then compared to the cement-void-spatial calibration curve for that void space amount, thereby allowing a determination of the location of the volumetric void space at one or more target depths. Thereafter, a physical image or visual depiction of the location can be established.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and from time to time. While a developer's efforts might be complex and time-consuming, such efforts would be, nevertheless, a routine undertaking for those of ordinary skill in the art having benefit of this disclosure.

It should be noted that when "about" is provided herein at the beginning of a numerical list, the term modifies each number of the numerical list, and does not exclude the precise number provided. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, numerical properties such as percentages, and so forth used in the present specification and associated claims are to be understood as being modified in all instances by the term "about." As used herein, the term "about" encompasses +/−5% of a numerical value. For example, if the numerical value is 80, the term "about" encompasses the range of 76 to 84. Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "substantially" means largely, but not necessarily wholly.

The use of directional terms such as above, below, upper, lower, upward, downward, left, right, uphole, downhole and the like are used in relation to the illustrative embodiments as they are depicted in the figures herein, the upward direction being toward the top of the corresponding figure and the downward direction being toward the bottom of the corresponding figure, the uphole direction being toward the surface of the well and the downhole direction being toward the toe of the well. Additionally, the embodiments depicted in the figures herein are not necessarily to scale and certain features are shown in schematic form only or are exaggerated or minimized in scale in the interest of clarity.

A wellbore HPF is established by taking a gamma spectrum from a cement column in a wellbore having a particular completion profile and at a target depth, obtaining a gamma spectrum from a standard for the same completion profile, and obtaining a correlation coefficient between the wellbore gamma spectrum and the standard gamma spectrum at the target depth. A cement quality curve is also established, wherein the cement quality curve represents a volumetric void space of the completion profile, which may be based on an actual reference wellbore, an electronically simulated wellbore, or a physically simulated wellbore (e.g., a laboratory built wellbore model having the completion profile), as discussed in greater detail below. The wellbore HPF is then compared to the cement quality curve to determine where on the cement quality curve the wellbore HPF falls, thereby permitting a determination of the cement volumetric void space in the wellbore cement column at the target depth.

The wellbore gamma spectrum used for determining the cement volumetric void space using HPF analysis may be additionally used to further determine the location of the cement volumetric void space in the wellbore at a target depth. In other embodiments, a separate wellbore gamma spectrum may be taken or obtained from the wellbore at a target depth, without departing from the scope of the present disclosure. As previously discussed, the wellbore penetrates a subterranean formation and has a completion profile comprising a pipe and an annulus between the pipe and the formation. A cement-void-spatial calibration curve is established based on obtained gamma spectra representing cement spatial void space locations in the annulus of the completion profile. Each cement volumetric void space amount in the annulus of the completion profile (e.g., in the wellbore) has its own characteristic cement-void-spatial calibration curve. The wellbore gamma spectrum and the cement-void-spatial calibration curve are then compared to determine a location of the cement volumetric void space within the annulus of the wellbore at the target depth, or at a plurality of target depths.

The wellbore gamma spectrum may be obtained using a downhole logging tool coupled to a conveyance extending into the wellbore. The downhole logging tool (which may also be referred to herein simply as a "logging tool") comprises a gamma source and a detector for obtaining a gamma spectrum of the wellbore at the target depth. A control system comprising a non-transitory medium readable for storing instructions for execution by a processor is coupled to the detector. The control system is capable of digitizing the wellbore gamma spectrum and determining a cement volumetric void space at one or more target depths within the wellbore. The control system is further capable of comparing the digitized wellbore gamma spectrum with a digitized cement-void-spatial calibration curve based on obtained gamma spectra representing cement spatial void space locations corresponding to the particular cement volumetric void space. Accordingly, the control system determines a location of the cement volumetric void space in the wellbore at the one or more target depths.

As described in greater detail herein, the control system may determine the cement volumetric void space at a target depth by digitizing the wellbore gamma spectrum, obtaining the correlation coefficient between it and one or more digitized standard gamma spectrum, thereby establishing the wellbore HPF, comparing the wellbore HPF to a digitized cement quality curve, and determining the volume of an unknown volumetric void space of cement disposed in the annulus of the wellbore at the target depth. In other embodiments, the control system may determine the cement volumetric void space by retrieval from a stored database for the particular wellbore or by manual input of the cement volumetric void space by an operator for the particular wellbore, without departing from the scope of the present disclosure. Additionally, one or more cement-void-spatial calibration curves may be electronically stored by the control system (e.g., in a database-like form) for use in the embodiments of the present disclosure, wherein the cement void-spatial calibration curves are characteristic of one or more particular cement spatial void space amount.

Referring now to FIG. 1, illustrated is a cross-sectional diagram of a cased wellbore 101 in a formation 104, according to one or more embodiments of the present disclosure. The wellbore 101 is lined with a casing string 102, wherein the casing string 102 may be a pipe, that may be formed from a hardened metal (e.g., steel) or plastic, for example. An annulus 105 is formed between the exterior of the casing string 102 and a wall of formation 104 (i.e., the wall of the wellbore). Cement 103 is introduced into the wellbore 101 through the interior of the casing string 102 such that upon reaching the bottom or the wellbore 101, it returns upward through the annulus 105 to cure and form a cement column. After curing, one or more volumetric void spaces, such as gap 106 may be located at a particular depth and relative location within the width of the cement column, thereby resulting in an area that is devoid of cement.

For example, the gap 106 may be formed due to imperfections introduced into the cement 103 during construction and/or due to subsequent wear damages caused by the use of the wellbore 101 (e.g., during hydrocarbon production). Using a downhole logging tool having a gamma source and a detector for obtaining a gamma spectrum of a wellbore at a target depth, in combination with the embodiments described herein of establishing a wellbore HPF and comparing it to a quality curve representing volumetric void spaces having the same completion profile as the wellbore, a volumetric void space of the amount of gap 106 can be determined. Upon determining the cement volumetric void space amount of gap 106, a downhole logging tool having a gamma source and a detector for obtaining a gamma spectrum of the wellbore at the target depth (or more than one target depth), in combination with the embodiments described herein of establishing a cement-void-spatial calibration curve for the particular amount of volumetric void space and comparing it to the wellbore gamma spectrum, the location of the volumetric void space can be determined within the annulus. The downhole logging tool for determining the volumetric void space of gap 106 and the location of the cement volumetric void space may be identical or different, provided that they comprise the components described herein including a gamma source and a detector and can be used in a subterranean formation environment. For example, the gamma sources may have differing energy ranges, without departing from the scope of the present disclosure, provided that overlapping energy ranges can be evaluated. An exemplary downhole logging tool is described with reference to FIG. 2 below.

Figure 2:
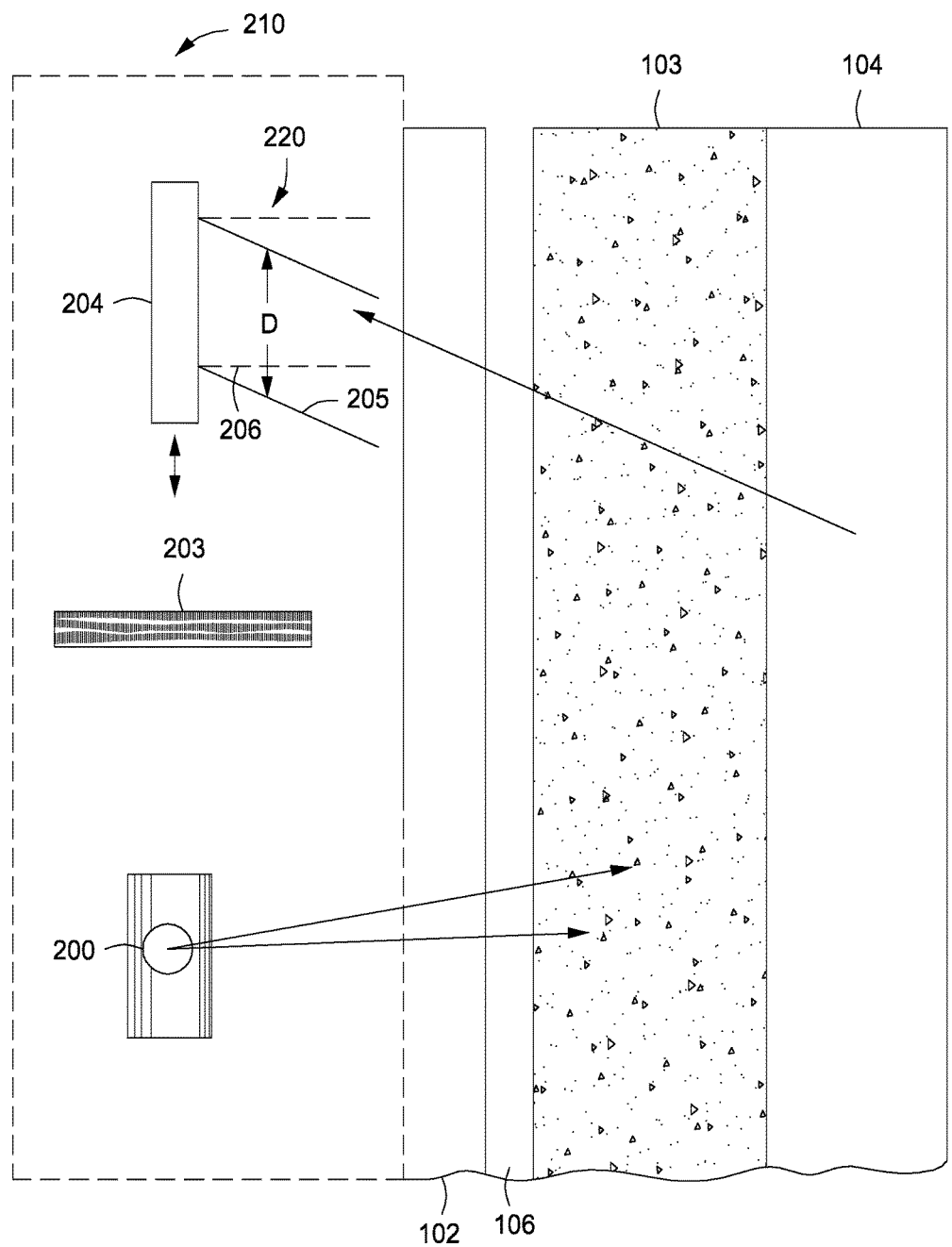
FIG. 2 is a block diagram of a downhole logging tool for performing one or more operation, according to one or more embodiments of the present disclosure.

Referring now to FIG. 2, illustrated is a block diagram showing a downhole logging tool 210, according to one or more embodiments of the present disclosure. The downhole logging tool 210 comprises a gamma source 200 for emitting gamma radiation, which penetrates the casing string 102, cement 103, and formation 104 and reflects back to the detector 204 to generate a gamma spectra associated with the cement 103 and possible gaps 106 inside or adjacent the cement 103 behind the casing string 102 and in the annulus 105 (FIG. 1), regardless of the location of any such gaps 106. The downhole logging tool may be located in a drill string tool housing to be used during a logging while drilling (LWD) or measurement while drilling (MWD) operation, or may be located in a wireline tool housing to be used during a wireline logging operation, or conveyed housed in any other downhole tool or by itself to a target location within wellbore 101 (FIG. 1), without departing from the scope of the present disclosure.

The gamma source 200 generates monochromatic high energy photon gamma radiation (i.e., gamma rays). The gamma source 200 may, for example, be a caesium-137 gamma radiation source. Photons from the gamma source 200 interact with the annulus 105 and any cement 103 or gaps 106 therein and back through the casing string 102 to the detector 204. The detector 204 thus detects the scattered photons from the gamma source 200 after the photons interact with the contents of the annulus 105.

A radiation shield 203 is located between the gamma source 200 and the detector 204. The radiation shield 203 blocks photons from traveling directly from the gamma source 200 to the detector 204 without passing through the annulus 105. The radiation shield 203 may be any photon blocking material (e.g., tungsten, lead, and the like) appropriate for blocking high energy photons from the gamma source 200. The front of the detector 204 may additionally be shielded with any material capable of acting as a photon blocking material (e.g., those used to form the radiation shield 203), such as a metal having a relatively high atomic number (e.g., tungsten) to block photons coming from scattering other than the annulus 105 and contents therein (or lack of contents). A detector collimator 220 (shown in phantom) may be cut into the detector 204 shielding to allow the photons scattered behind the casing string 102 to pass through. The size (e.g., diameter) "D" of the detector collimator 220, its relative position to a detector crystal and its angle (if any) relative to the gamma source 200 may determine the amount of gamma rays (i.e., photons) detected by the detector 204. The amount of photons may be represented by a graphical depiction of detection rate (i.e., counts per second, such as per 5 seconds).

In one embodiment, a detector collimator 205 may be angled more toward the gamma source 200 than toward the formation 104. In another embodiment, a detector collimator 206 may be angled more toward the formation 104 than toward the gamma source 200. The detector collimator 220 may also have various sizes D in order to detect desired energy spectra, without departing from the scope of the present disclosure. In order to provide a more desirable energy range within which the detected energy spectra is independent of the formation 104, the energy range may be increased in response to the detector collimator (e.g., 205 or 206) being angled more toward the gamma source 200. In another example, the energy range may be increased in response to decreasing the diameter D of the detector collimator.

The energy range for any particular gamma source 200 for use in the embodiments described herein is determined based on the nature of the gamma source 200 itself. For example, the energy range shown in FIGS. 4-5 and 9-10 is from 0 keV to 600 keV, although other ranges are contemplated, without departing from the scope of the present disclosure and which depend on the particular gamma source 200. A particular energy range within the full gamma spectrum of the gamma source 200 may be selected according to the embodiments herein for evaluation or manipulation to determine information about cement quality, such as to compute one or more HPF values or to determine the location of one or more cement volumetric void spaces. That is, a more narrow range is selected for processing the scattered photons received by the detector 204, or the detector may be designed to receive a more narrow range.

This energy range for processing the data described herein will be referred to as "the energy range for processing" or the "processing energy range," and grammatical variants thereof. For example, in some embodiments, the energy range for processing related to determining cement volumetric void space amount (e.g., HPF) may be in the range of from about 250 kiloelectron volts (keV) to about 500 keV, encompassing any value and subset therebetween. For example, the energy range for processing related to determining cement volumetric void space amount (e.g., HPF) may be of from about 250 keV to about 300 keV, or about 300 keV to about 350 keV, or about 350 keV to about 400 keV, or about 400 keV to about 450 keV, or about 450 keV to about 500 keV, encompassing any value and subset therebetween. The processing energy range for the cement-void-spatial calibration curve, as discussed in greater detail below, may be the same or different as the processing energy range for determining the HPF or cement quality curve. In some embodiments, the processing energy range for forming the cement-void-spatial calibration curve is in the range of about 150 keV to about 250 keV, encompassing any value and subset therebetween. For example, the processing energy range for forming the cement-void-spatial calibration curve may be in the range of about 150 keV to about 170 keV, or about 170 keV to about 190 keV, or about 190 keV to about 210 keV, or about 210 keV to about 230 keV, or about 230 keV to about 259 keV, encompassing any value and subset therebetween. Each of these values is critical to the embodiments of the present disclosure and may depend on a number of factors including, but not limited to, the configuration of the logging tool 210 (e.g., the angle of the detector collimator), the energy spectra used to establish the cement quality curve, the energy spectra used to establish the standard gamma spectrum, the amount of cement volumetric void space, the design of the completion profile, and the like, and any combination thereof. Accordingly, the HPF and/or the cement-void-space calibration curves described herein may be computed based on a gamma spectrum within this range as described in more detail below.

As defined herein, a detector collimator 205 that is "angled more toward the formation" has an angle of approximately 90° with reference to the longitudinal axis of the logging tool 210. As used herein, a detector collimator 205 that is "angled more towards the gamma source" has an input having an angle of less than, or substantially less than, 90° with reference to the longitudinal axis of the logging tool 210. The distance between the detector 204 and the gamma source 200 may be adjusted, in addition to adjusting the collimator angle and/or the collimator diameter D, to detect and evaluate gamma ray energy spectra within a processing energy range, (e.g., between about 250 keV and 500 keV, or between about 150 keV and 250 keV).

The energy spectra received by the detector 204 are independent of the formation 104 properties (e.g., porosity, density, permeability, and the like). Accordingly, the received energy spectra are substantially similar (e.g., amplitude and shape) even as the formation 104 properties change (e.g., porosity, and the like), and may depend on other factors including, but not limited to, various tool design parameters (e.g., detector-to-source distance, collimator angle, collimator diameter, and the like). In some embodiments, during a logging operation, the logging tool 210 may be placed against the casing string 102 in the wellbore 101 in order to reduce or eliminate any space between the logging tool 210 and the casing string 102 that may alter spectral measurements.

Photons entering the annulus 105 from the gamma source 200 may be reflected back through interaction with contents of the annulus 105 (i.e., cement 103 and/or gaps 106) at a single depth, or at a plurality of depths. Additionally, the logging tool 210 may interact with the wellbore 101 at a single location or at multiple locations, such as by rotating the logging tool 210 in the azimuthal direction in the wellbore 101 at a single depth so that an entire diameter of the annulus 105 is investigated.

Accordingly, as described above, the design parameters for the logging tool 210 include detector-to-source spacing, detector collimator size, and detector collimator angle. The optimal logging tool 210 design parameters increase spectrum count rates, increase spectrum sensitivity to cement 103 quality, and decrease the spectrum sensitivity to formation 104 properties.

Figure 3:
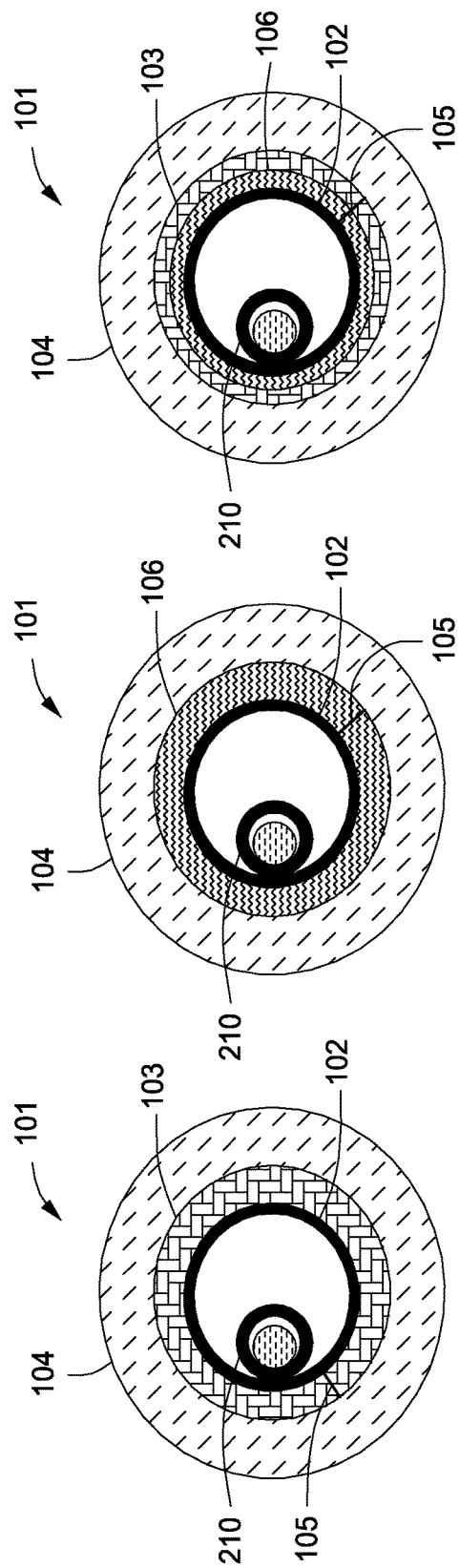
FIGS. 3A-3C are diagrams showing various wellbore configurations for use in determining the wellbore heterogeneity profiling factor, according to one or more embodiments of the present disclosure.

Referring now to FIGS. 3A-3C, with continued reference to FIGS. 1 and 2, illustrated is a logging tool 210 for use in establishing a wellbore gamma spectrum for determining a wellbore HPF, where the annulus may have full cement, no cement, or cement with gaps therein. Referring now to FIG. 3A, wellbore 101 comprises subterranean formation 104, casing string 102, and annulus 105. Within the annulus 105 is cement 103, which has no gaps, or no detectable gaps, therein. Accordingly, the wellbore 101 is referred to as "well-bonded," as cement 103 fully fills the annulus 105 between the casing string 102 and the formation 104. Downhole logging tool 210 is shown abutted to the casing string 102 for emitting gamma rays and receiving an energy spectrum therefrom associated with the volumetric space of the cement 103, which in FIG. 3A does not comprise any, or any detectable, void space therein. FIG. 3B, on the other hand, shows a wellbore 101 comprising subterranean formation 104, casing string 102, and annulus 105. The annulus 105 comprises gap 106 and no cement. Such a wellbore 101 is referred to as "free-pipe," as the annulus 105 has no cement therein. The annulus 105 may be filled with some other substance, including a gas (e.g., air) or a fluid (e.g., water).

In many wellbores, the annulus, however, is neither well-bonded nor free-pipe, but instead comprises both gaps and cement, as shown in FIG. 3C. FIG. 3C depicts a wellbore 101 comprising subterranean formation 104, casing string 102, and annulus 105. Within the annulus 105 is both cement 103 and gap 106. As depicted, the gap 106 abuts the casing string 102 and is continuous about the diameter of the annulus 105. It will be appreciated, however, that the gap 106 may be discontinuous (i.e., a plurality of gaps) that may be positioned at any location in the annulus 105 (e.g., closer to the formation 104), without departing from the scope of the present disclosure. Additionally, the gap 106 may be filled with some other fluid, including a gas (e.g., air) or a fluid (e.g., water). Accordingly, locating the logging tool 210 at a depth in the wellbore 101 and obtaining energy spectra from the entire diameter about the casing string 102 representing the annulus therein may be preferred.

Accordingly, the wellbore gamma spectrum for use in determining the wellbore HPF of the present disclosure may be taken at a target depth in a wellbore being examined for cement volumetric void space (an "examined wellbore") having a particular completion profile, as described above. Moreover, the wellbore gamma spectrum taken for determining the wellbore HPF may be used to evaluate the location of the cement volumetric void space as further described below because the wellbore gamma spectrum is not only correlated to a volumetric void space amount (determined using the HPF and quality curve), but also a location of the volumetric void space.

Referring again to the HPF analysis, a gamma spectrum from a standard (a "standard gamma spectrum") having the same completion profile is also obtained. The standard gamma spectrum is obtained from a free-pipe or well-bonded actual or simulated wellbore having an identical completion profile as that of the examined wellbore. That is, the standard wellbore may be simulated using a computer having a non-transitory medium and a processor, such as by Monte Carlo simulation, which uses computational algorithms to obtain a model of the standard wellbore. In other embodiments, the standard wellbore may be physically simulated, where a physical model of the standard wellbore is created in a laboratory setting. In yet other embodiments, a section of the examined wellbore or an actual wellbore having the completion profile of the examined wellbore may be used where it is known that it is a free-pipe actual wellbore or a well-bonded actual wellbore, such as by logging experiments performed on the actual wellbore. Thus, the standard gamma spectrum may be obtained from a free-pipe standard or a well-bonded standard based on an electronically simulated wellbore, a physically simulated wellbore, or an actual reference wellbore having the same completion profile as the examined wellbore or a section of the examined wellbore, according to the embodiments described herein. Various standard gamma spectra may be gathered and recorded manually or electronically stored in a database-like medium for retrieval and use based on completion profiles for use in obtaining the wellbore HPF. That is, in some embodiments, the standard gamma spectrum may be based on prior physical or simulated wellbores such that another standard gamma spectrum need not be obtained.

The wellbore and standard gamma spectra used to calculate the HPF described herein may be obtained within an identically defined energy range, which may be the processing energy range (i.e., narrowed from a full energy range) described above of from about 250 keV to about 500 keV, encompassing any value and subset therebetween. That is, the processing energy range used to analyze the wellbore and standard gamma spectra are the same, allowing further analysis of the two spectra, as described in greater detail below.

The wellbore HPF is finally computed by obtaining a correlation coefficient between wellbore gamma spectrum at the target depth and the standard gamma spectrum. As used herein, the term "correlation coefficient" means a statistical measure of the degree to which changes to the value of one variable predict change to the value of another. The method of determining the correlation coefficient between the wellbore gamma spectrum and the standard gamma spectrum is not limiting to any particular method, but rather any method of obtaining a correlation coefficient between the wellbore and standard gamma spectra can be used in accordance with the methods of the present disclosure. For example, the correlation coefficient may be obtained based on the total detected photon count rates, the energy spectra shape, and/or the energy spectra amplitude of the wellbore and standard gamma spectra.

The value of the correlation coefficient is the HPF for the examined wellbore at the target depth. As previously stated, a plurality of target depths may be evaluated throughout a length of a wellbore, without departing from the scope of the present disclosure. Indeed, in doing so, an operator may determine the quality (e.g., integrity) of the cement column throughout the entire length of the examined wellbore, which may prompt corrective actions (e.g., a cement squeeze operation) or warrant abandonment of the wellbore to avoid environmental or human hazards.

Figure 4:
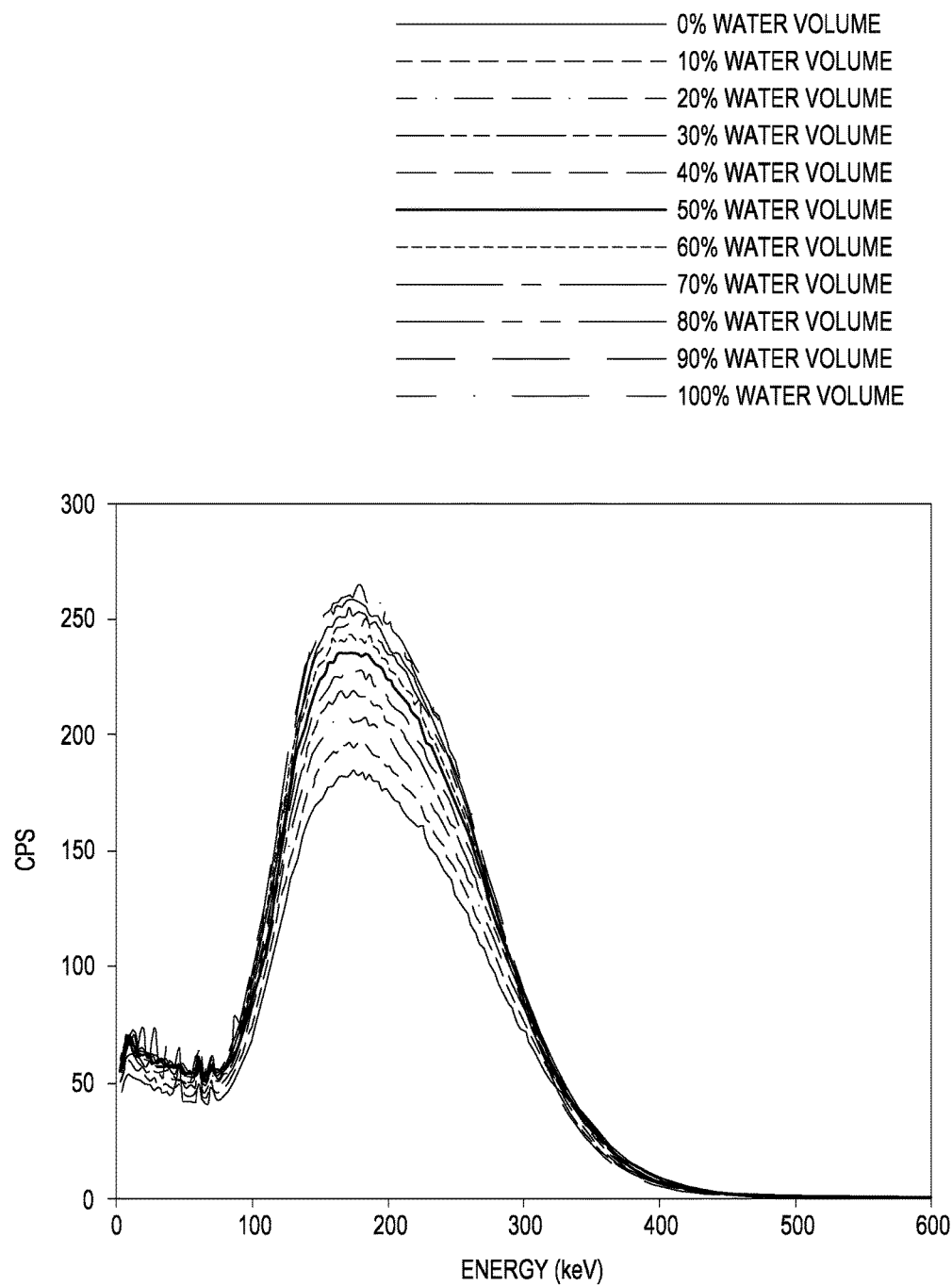
FIG. 4 is a graph showing detected gamma energy spectra for use in forming a cement quality curve, according to one or more embodiments of the present disclosure.
Figure 5:
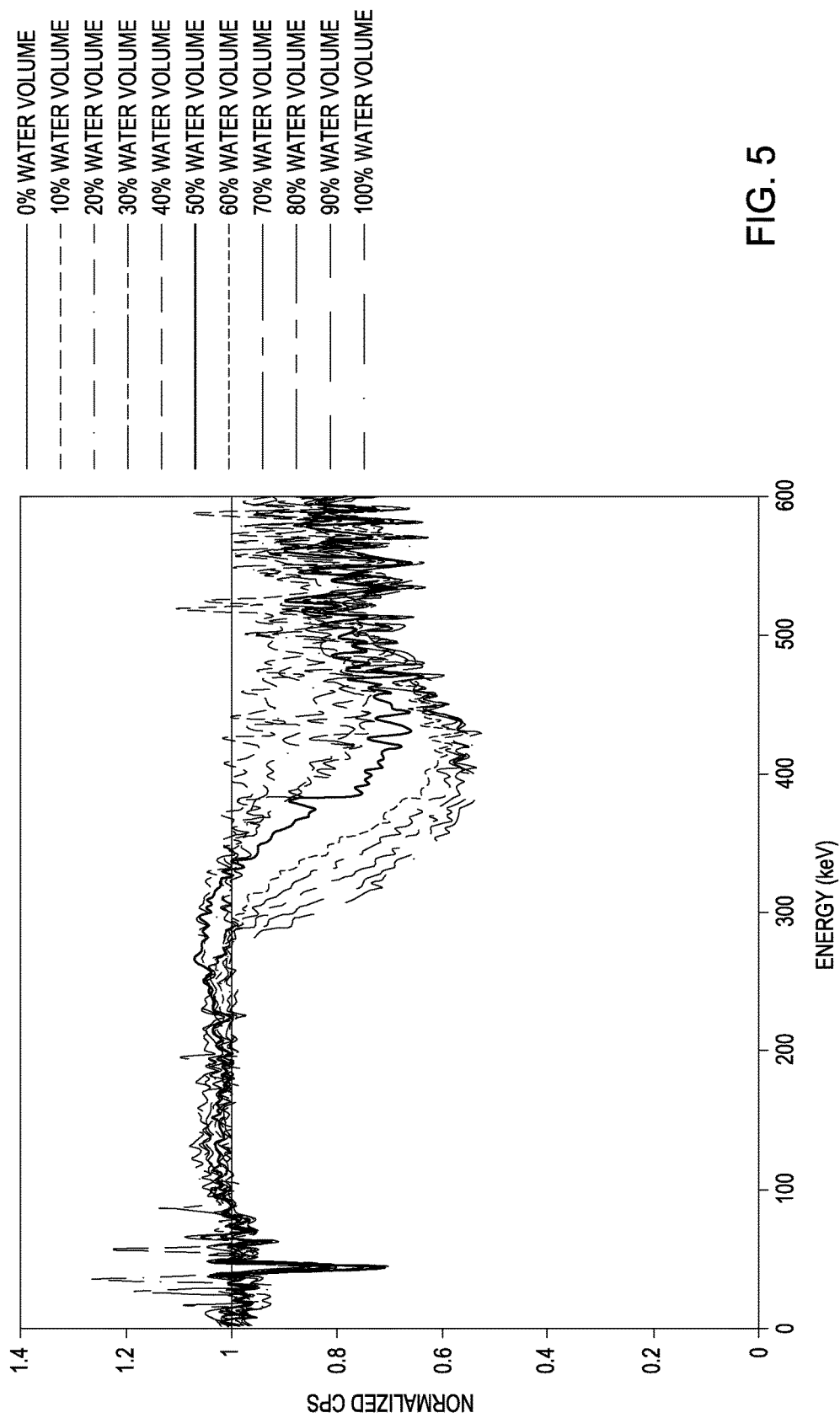
FIG. 5 is a graph showing normalized detected gamma energy spectra for use in forming a cement quality curve, according to one or more embodiments of the present disclosure.

As a specific example, the wellbore HPF may be obtained based on two standard gamma spectra, which is also depicted in FIGS. 4 and 5 with reference to the cement quality curve below. A free-pipe standard gamma spectrum and a well-bonded gamma spectrum are obtained having the completion profile of the examined wellbore of interest. Thereafter, the correlation coefficient is obtained by normalizing the wellbore gamma spectrum and the two standard spectra. As used herein, the term "normalized," and grammatical variants thereof (e.g., "normalizing," "normalization," and the like), refers to mathematical multiplication of a gamma spectrum (e.g., based on a detected photon count rate, an energy spectra shape, or an energy spectra amplitude) by a factor that makes a selected value thereof an integral equal to a desired value. The desired value for normalization may be 1, for example. The spectra may be normalized to have the same total count rates across the entire detected (or processing) energy range for any one of the wellbore gamma spectrum, the free pipe standard gamma spectrum, or the well-bonded standard gamma spectrum. The normalized spectra are then divided by the normalized free-pipe gamma spectrum. Thereafter, the correlation coefficient is determined using the Formula I:

$$\frac{\sum (x-\bar{x})(y-\bar{y})}{\sqrt{\sum (x-\bar{x})^2 \sum (y-\bar{y})^2}},$$

where x represents the normalized wellbore gamma spectrum and y represents the normalized well-bonded standard gamma spectrum. Alternatively, after normalizing the wellbore gamma spectrum, the free-pipe gamma spectrum, and the well-bonded gamma spectrum, the normalized spectra are divided by the normalized well-bonded gamma spectrum and the correlation coefficient is determined using Formula I, where x represents the normalized wellbore gamma spectrum and y represents the normalized free-pipe standard gamma spectrum.

Once the wellbore HPF for the wellbore is obtained, it is compared to a cement quality curve. As used herein, the term "cement quality curve" refers to a collection of HPF values having known cement volumetric void amounts and a known completion profile. The cement quality curve is established using an electronically simulated wellbore or a physically simulated wellbore having the same completion profile as the examined wellbore; that is, having the same completion profile as the actual wellbore an operator is seeking to determine the cement volumetric void space therein. The electronically or physically simulated wellbore for use in forming the cement quality curve may be by any means discussed above with reference to obtaining the standard cement quality curve (e.g., by electronic modeling such as Monte Carlo simulation, physical modeling in a laboratory setting, and the like). The chosen gamma spectra are selected within a defined processing energy range, such as the same range as the wellbore gamma spectrum and the standard gamma spectrum discussed above, and an HPF is obtained by obtaining a correlation coefficient between the gamma spectra with known cement volumetric void space and either a cement-only (or well-bonded) standard and a no-cement (or free-pipe) standard.

For example, the cement quality curve may be obtained by creating a plurality of electronic or physically simulated wellbores having the completion profile of the examined wellbore. Each of the simulated wellbores as an annulus having a known thickness. As used herein, the term "thickness" with reference to a completion profile refers to the annular distance between a pipe, such as a casing string, and a formation surface. In establishing the cement quality curve, the simulated wellbores are characterized at least by the thickness (t) of the annulus and a void resolution thickness percentage (p %). As used herein, the term "void resolution thickness percentage" refers to a known percentage of volumetric void space within an annulus of a simulated wellbore. For example, a physically simulated wellbore may be modeled in a laboratory setting, having a completion profile and an annulus of a known thickness. The annulus may be packed 50% with cement against the simulated formation, and 50% with a different material against the simulated casing string, such as air, water, mud, or another gas or fluid, similar to FIG. 3C. In such an example, the void resolution thickness percentage (p %) would equal 50%. As another example, the annulus may be packed 80% with cement against the simulated formation and 20% with a different material against the simulated casing string, where p %=20%. Equally applicable would be any simulated wellbores created electronically.

One of the simulated wellbores represents a cement-only thickness, where (t) has 100% cement; the cement-only thickness simulated wellbore may also be referred to as well-bonded, as described above. Another of the simulated wellbores represents a no-cement thickness, where (t) has 0% cement; the no-cement thickness simulated wellbore may also be referred to as free-pipe, as described above. One or more cement-void thickness simulated wellbores are then created to represent at least one known p %. The one or more cement-void thickness simulated wellbores may be established using Formula II: (t)*(n)(p %), where n represents an integer between 1 and 1/(p %)−1. For example, a plurality of cement-void thickness simulated wellbores may be created where p % is in 1% increments, or 5% increments, or 10% increments, or 20% increments, or 30% increments, or 40% increments, or 50% increments, encompassing any value or subset therebetween. Smaller increments may additionally be used, without departing from the scope of the present disclosure. Moreover, the one or more cement-void thickness simulated wellbores need not be in even increments. For example, two cement-void thickness simulated wellbores may be prepared (e.g., where p %=30% and 80%, or where p %=40% and 60%, and the like). The remaining p % values can be extrapolated therefrom and based on the no-cement and cement-only thickness simulated models.

With continued reference to FIGS. 3A-3C, illustrated are wellbores having logging tool 210 therein for determining cement volumetric void thickness. These wellbores also illustrate simulated wellbores that can be used to form the cement quality curve described herein. For example, FIG. 3A illustrates a cement-only thickness simulated wellbore, FIG. 3B illustrates a no-cement thickness simulated wellbore, and FIG. 3C illustrates a cement-void thickness simulated wellbore. As previously mentioned, the volumetric void space within the annulus 105 of the cement-void thickness simulated wellbore may be at any location throughout the annular thickness of the annulus 105, including in multiple discontinuous locations or a single continuous void space, without departing from the scope of the present disclosure.

Upon establishing the cement-only thickness simulated wellbore, the no-cement thickness simulated wellbore, and the at least one cement-void thickness simulated wellbore, a gamma spectrum is obtained for each simulated wellbore. Referring now to FIG. 4, illustrated is a graph depicting a series of gamma energy spectra obtained for use in forming the cement quality curve described herein. The simulated wellbores used to establish the gamma spectra in FIG. 4 used water to simulate void space within an annulus having a particular completion profile. Accordingly, the 0% water volume spectra represents the cement-only thickness simulated wellbore and the 100% water volume spectra represents the no-cement thickness simulated wellbore. Therebetween are nine spectra representing 10% void space increments from cement-void thickness simulated wellbores. The defined energy range, in which the simulated wellbores are evaluated, as shown, is in the range of 0 keV to 600 keV. Accordingly, the defined energy range for forming the cement quality curve may be in the range of about 0 keV to about 600 keV, encompassing any value and subset therebetween. In some embodiments, for example, the range may be a processing energy range (i.e., a more narrow energy range compared to the full energy range a gamma source can emit) of from about 250 keV to about 500 keV, encompassing any value and subset therebetween. As can be seen in FIG. 4, the photon counts per second (CPS) along the y-axis increases with increasing volumetric void space (i.e., decreased volume of cement) within the annulus of the simulated wellbores.

A correlation coefficient is obtained between the at least one cement-void thickness gamma spectrum and the cement-only thickness gamma spectrum, or between the at least one cement-void thickness gamma spectrum and the no-cement thickness gamma spectrum. As used herein, the term "thickness gamma spectra" collectively refers to the at least one cement-void thickness gamma spectrum, the cement-only thickness gamma spectrum, and the no-cement thickness gamma spectrum. Any method of determining the correlation coefficient discussed above with reference to establishing the wellbore HPF of an examined wellbore may be used to establish the cement quality curve, without departing from the scope of the present disclosure. The correlation coefficient(s) thus establishes various quality curve HPF values.

As a specific example, similar to that described with reference to establishing the wellbore HPF, the correlation coefficient for use in forming the cement quality curve may be determined using Formula I. For example, the thickness gamma spectra may be normalized to have the same count rates in the entire energy range for the one or more cement void gamma spectrum, the no-cement thickness gamma spectrum, or the cement-only thickness gamma spectrum, without departing from the scope of the present disclosure.

The at least one normalized cement-void thickness gamma spectrum and the normalized no-cement thickness gamma spectrum is then divided by the normalized cement-only thickness gamma spectrum, as illustrated in FIG. 5. Thereafter, the correlation coefficient is determined using the Formula I:

$$\frac{\sum (x-\bar{x})(y-\bar{y})}{\sqrt{\sum (x-\bar{x})^2 \sum (y-\bar{y})^2}},$$

where x represents the normalized at least one cement-void thickness gamma spectrum and y represents the normalized no-cement thickness standard gamma spectrum. Alternatively, after normalizing the thickness gamma spectra, the at least one normalized cement-void thickness gamma spectrum and the normalized cement-only thickness gamma spectrum are then divided by the normalized no-cement thickness gamma spectrum, and the correlation coefficient is determined using Formula I, where x represents the normalized cement-void thickness gamma spectrum and y represents the normalized cement-only thickness gamma spectrum.

Figure 6:
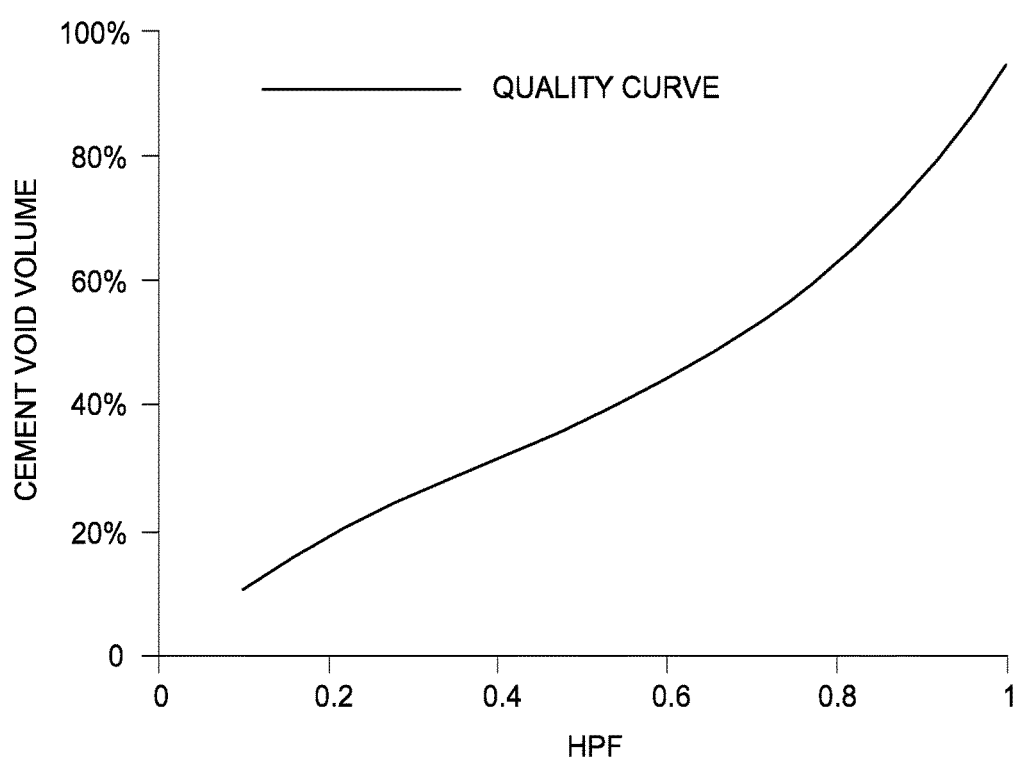
FIG. 6 is a graph of a cement quality curve, according to one or more embodiments of the present disclosure.

Referring now to FIG. 6, illustrated is a cement quality curve for determining the volumetric void space of a cement column in an annulus in the examined wellbore(s). The cement quality curve was established using the HPF values computed from FIGS. 4 and 5. One or more wellbore HPFs (not shown) may be compared to the cement quality curve, each at one or more depths or circumferential locations within a single wellbore, for example, thereby linking wellbore HPF value(s) to a particular cement volumetric void space using a particular completion profile. Accordingly, wellbore HPFs having an unknown cement volumetric void space at a particular location or depth within an examined wellbore may be plotted against the cement quality curve to determine the percentage of cement volumetric void space in the examined wellbore at that location or depth.

Additionally, multiple quality curves can be established based on different wellbore completion profiles. After obtaining the wellbore gamma spectrum and the standard gamma spectrum to determine a correlation coefficient between the two spectra, as described above, to establish the HPF, advanced mathematical analysis methods, such as wavelet analysis, neural network training, basis functions, and the like, may be applied to evaluate cement volumetric void space within an examined wellbore.

Figure 7A:
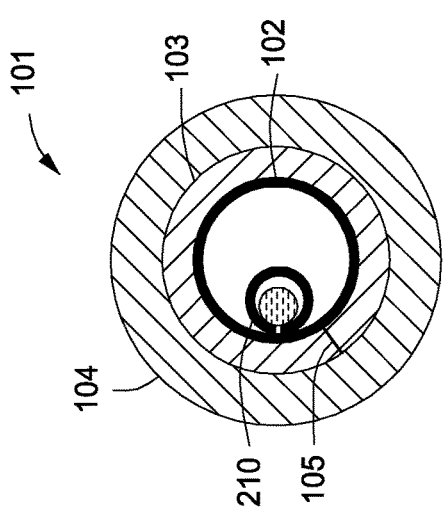
FIGS. 7A-7C are diagrams showing various wellbore configurations depicting locations of cement volumetric void space therein, according to one or more embodiments of the present disclosure.
Figure 7B:
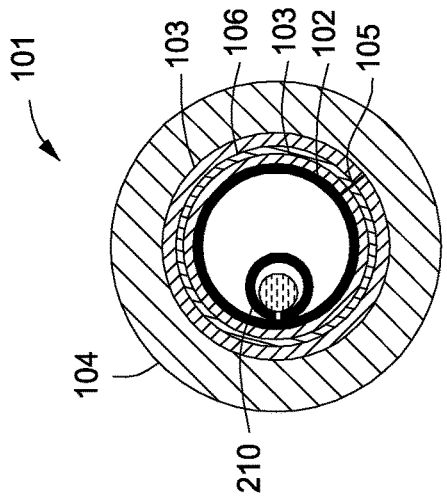
Figure 7C:
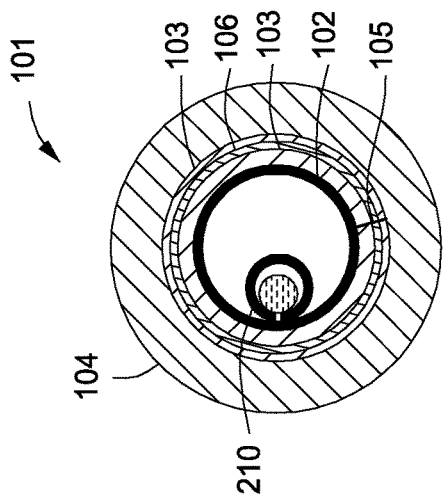

Referring now to FIGS. 7A-7C, with continued reference to FIGS. 1 and 2, illustrated is a logging tool 210 for use in establishing a wellbore gamma spectrum, which may be substantially similar to downhole logging tool 210 of FIG. 2, where the annulus may have full cement, a single gap at a first location, or a single gap at a second location that is different from the first location. Referring now to FIG. 7A, wellbore 101 comprises subterranean formation 104, casing string 102, and annulus 105. Within the annulus 105 is cement 103, which has no gaps, or no detectable gaps, therein. Accordingly, the wellbore 101 is referred to as well-bonded, as described above. For the same reasons, such well-bonded wellbores may additionally be referred to as having a "cement-only thickness." Downhole logging tool 210 is shown abutted to the casing string 102 for emitting gamma rays and receiving an energy spectrum therefrom associated with determining a location of a volumetric void space, although in FIG. 7A no void space, or no detectable void space, would be detected.

FIGS. 7B and 7C, on the other hand, show wellbores 101 having both gaps 106 and cement 103. Notably, however, the location of gap 106 (i.e., cement volumetric void space) is in a different location in FIGS. 7B and 7C. In FIG. 7B, the gap 106 is sandwiched between cement 103 in the annulus 105 closer to the casing string 102. In FIG. 7C, the gap 106 is sandwiched between cement 103 in the annulus 105 closer to the subterranean formation 104 and away from the casing string 102, relative to FIG. 7B. It will be appreciated, that the gap 106 may be located at any position within the annulus 105, including abutting to casing string 102, sandwiched anywhere between the cement 103, or abutting the formation 104, and have any width within the confines of the width of the annulus 105. Moreover, as depicted in FIGS. 7B and 7C, the gap 106 is continuous about the diameter of the annulus 105. It will be appreciated, however, that the gap 106 may be discontinuous (i.e., a plurality of gaps) that may be positioned at any location in the annulus 105 (e.g., closer to the formation 104, closer to the casing string 102, and the like), without departing from the scope of the present disclosure. Accordingly, locating the logging tool 210 at a depth in the wellbore 101 and obtaining energy spectra from the entire diameter about the casing string 102 representing the annulus therein may be preferred. The gap 106 may be filled with some other fluid, including a gas (e.g., air) or a fluid (e.g., water).

Accordingly, the wellbore gamma spectrum for use in determining the location of a cement volumetric void space of the present disclosure may be taken at a target depth in a wellbore being examined for such location (an "examined wellbore," which may be taken simultaneously or at a different time as the examined wellbore gamma spectrum pertaining to HPF) having a particular completion profile, as described above. Indeed, the wellbore gamma spectrum taken for determining the wellbore HPF may be used to evaluate the location of the cement volumetric void space as further described below because the wellbore gamma spectrum is not only correlated to a volumetric void space amount (determined using the HPF and quality curve), but also a location of the volumetric void space. Accordingly, in some embodiments, the cement volumetric void space for use in determining the location thereof is determined based on a wellbore HPF and a cement quality curve, or simply an earlier gamma spectrum obtained from the examined wellbore of interest at the target depth.

Once the cement volumetric void space for a particular wellbore at a particular target depth or depths is obtained (e.g., by using HPF analysis, and the like), it is compared to a cement-void-spatial calibration curve. The cement-void-spatial calibration curve is established based on a plurality of obtained gamma spectra representing cement spatial void space locations in the annulus of a completion profile. As previously discussed, each cement-void-spatial calibration curve is based on a specific volumetric void space amount. That is, each cement volumetric void space amount has a characteristic cement-void-spatial calibration curve for a known completion profile.

The cement-void-spatial calibration curve may be established using an electronically simulated wellbore or a physically simulated wellbore having the same completion profile as the examined wellbore; that is, having the same completion profile as the actual wellbore an operator is seeking to determine the location of the cement volumetric void space therein. The electronically or physically simulated wellbore for use in forming the cement-void-spatial calibration curve may be by any means discussed above with reference to obtaining the standard cement quality curve (e.g., by electronic modeling such as Monte Carlo simulation, physical modeling in a laboratory setting, and the like). The chosen gamma spectra are selected within a defined processing energy range, such as in the range of about 150 keV to about 250 keV, encompassing any value and subset therebetween. The gamma spectra for use in forming the cement-void-spatial calibration curve may be based on detected photon count rates, energy spectra shapes, or energy spectra amplitudes within the wellbore gamma spectrum (e.g., the about 150 keV to about 250 keV, where the wellbore gamma spectrum was taken using a gamma source 200 (FIG. 2) having an energy range of from 0 keV to 600 keV, or other range). In other embodiments, the gamma spectra for use in forming the cement-void-spatial calibration curve may be based on normalized detected photon count rates, normalized energy spectra shapes, or normalized energy spectra amplitudes within the wellbore gamma spectrum, without departing from the scope of the present disclosure.

For example, the cement-void-spatial calibration curve may be obtained by creating a plurality of electronic or physically simulated wellbores having the completion profile of the examined wellbore. Each of the simulated wellbores as an annulus having a known thickness. As previously stated, the term "thickness" with reference to a completion profile refers to the annular distance between a pipe, such as a casing string, and a formation surface. In establishing the cement-void-spatial calibration curve, the simulated wellbores are characterized at least by the thickness (t) of the annulus and a spatial resolution thickness (x). As used herein, the term "spatial resolution thickness" refers to a ratio of void thickness to cement thickness (void thickness: cement thickness) in the annulus of a wellbore having a particular completion profile and corresponds to the cement volumetric void space amount in the wellbore. For example, a physically simulated wellbore may be modeled in a laboratory setting, having a completion profile, an annulus of a known thickness, and a cement volumetric void space of 10%. Accordingly, 90% of the annular volume of the annulus comprises cement and 10% comprises a different material, such as air, water, mud, or another gas or fluid, similar to FIGS. 7B and 7C. In such an example, the spatial resolution thickness ratio (x) would equal 0.1. As another example, the annulus may have a cement volumetric void space of 30%, such that 70% of the annular volume of the annulus is packed with cement and 20% is packed with a different material, where (x)=0.3. Equally applicable would be any simulated wellbores created electronically.

Referring now to FIGS. 8A-8D, with continued reference to FIGS. 1, 2, and 7A-7B, illustrated are diagrams showing various simulated wellbore configurations for use in forming a cement-void-spatial calibration curve, according to one or more embodiments of the present disclosure. FIGS. 8A-8D demonstrate cement void positions using the spatial resolution thickness (x), as described above. As used herein, the term "cement void positions," which may qualify particular types thereof (e.g., "cement-only cement void position," "first spatial-void cement void position," "second spatial-void cement void position," and the like), and grammatical variants thereof, refers to the position of a cement volumetric void space in an annulus relative to a casing string.

Figure 8A:
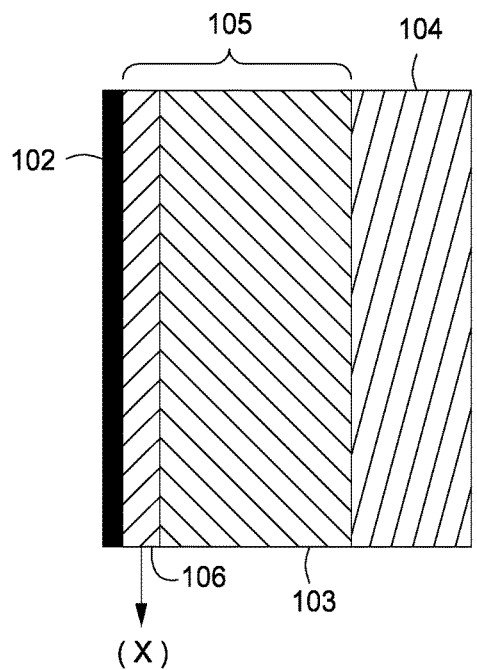
FIGS. 8A-8D are diagrams showing various simulated wellbore configurations for use in forming a cement-void-spatial calibration curve, according to one or more embodiments of the present disclosure.

Referring now to FIG. 8A, a first spatial-void thickness simulated wellbore is created where the first spatial-void thickness gap 106 is adjacent to the casing string 102 (i.e., the pipe) and is equal to (t)*(x). That is, the first spatial-void thickness gap 106 (and those that will follow) is equal to a known cement volumetric void space, such as one determined using HPF analysis for the examined wellbore. As used herein, the term "adjacent to" refers to a position that is in contact with or otherwise abutting another location within the annulus, including in contact with the pipe or casing string 102 and the formation 104. Accordingly, as shown in FIG. 8A, the first spatial-void thickness gap 106 equal to (t)*(x) is adjacent to the casing string 102, and has cement 103 extending and contacting the formation in a direction away from the casing string 102. The first spatial-void cement void position is assigned a value of 0. This value represents the initial position of the void space being adjacent to the casing string 102. That is, regardless of the thickness of the first spatial-void thickness gap 106, which is equal to (t)*(x), the initial cement void position is assigned a value of 0. The position of each cement void is defined by the spatial-void cement void position and the adjacent cement void position closer to the casing string 102.

Figure 8B:
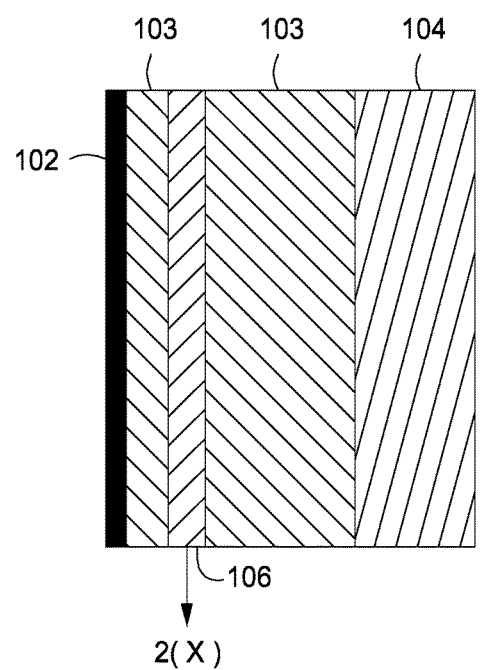
Figure 8C:
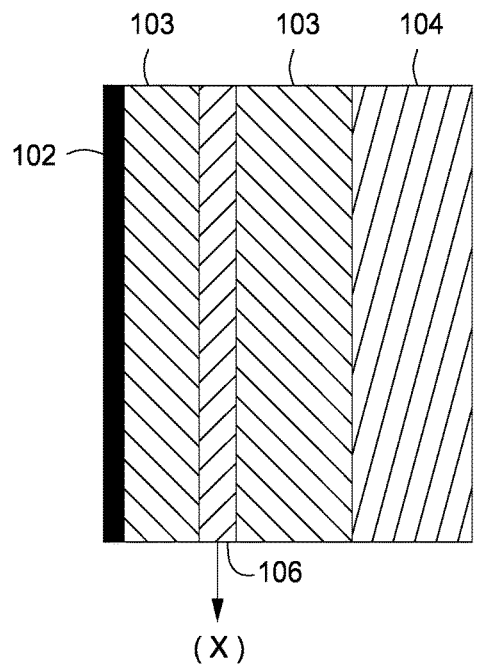
Figure 8D:
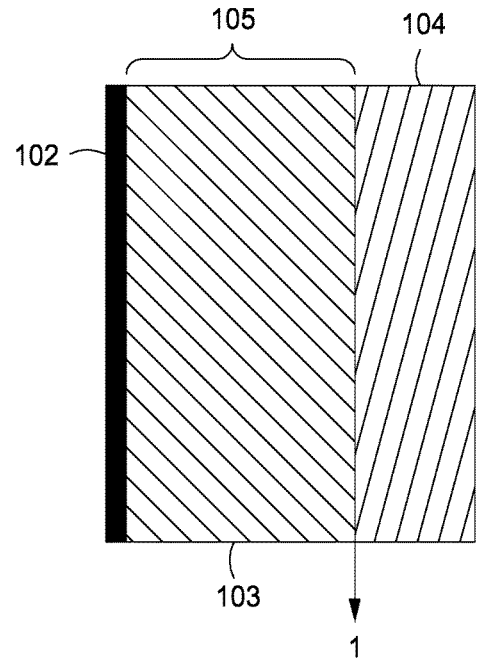

Referring now to FIG. 8B, at least a second spatial-void thickness simulated wellbore is created where the at least one second spatial-void thickness gap 106 is adjacent to the first spatial-void thickness toward the subterranean formation 104 and away from the casing string 102, such that the at least one second spatial-void thickness is surrounded by cement 103. The at least second spatial-void thickness is of the same thickness (t)*(x) as the first spatial-void thickness. The at least second spatial-void thickness, and any subsequent spatial-void thickness simulated wellbores are moved toward the formation 104. The spacing between the second spatial-void thickness and the casing string 102 is defined according to the Formula: (t)*(n)*(x), where n represents an integer between 1 and 1/(x). Accordingly, as shown in FIG. 8B, the gap 106 is equivalent in amount of (x), and is located at a distance away from the casing string of (t)*(x), and the subsequent spatial-void thickness simulated wellbore gap 106 in FIG. 8C is equivalent in amount to (t)*(x) but is located at a distance away from the casing string of 2*(t)*(x). Accordingly, the at least second spatial-void cement void position is equivalent to a value of (n)*(t)*(x). As an example, if the simulated wellbores having greater than the second spatial-void thickness gap 106 are thus continuously increased in distance as provided above until n=1/(x) and only cement 103 is located in the annulus 105, as shown in FIG. 8D; such a cement void position is thus equal to a value of 1.

As an example, (x) may be 0.5, where only a first spatial-void thickness and a second spatial-void thickness simulated wellbore are created. In such cases, the first spatial-void cement void position has a value of 0 and the second spatial-void cement position is 0.5. The cement-only cement void position (i.e., no cement void) finally has a value of 1, such as in FIG. 8D. On the other hand, (x) may be 0.1, where a first spatial-void thickness is created followed by nine additional spatial-void thickness simulated wellbores, each representing a 10% cement volumetric void space thickness at ten different cement void positions throughout the annular thickness of the annulus 105. Accordingly, the first spatial-void cement void position is 0, the second spatial-void cement position is 0.1, the third spatial-void cement position is 0.2, the fourth spatial-void cement void is 0.3, and so on until there are is no cement void space and thus n=1/(x) and has a value of 1. In another example, (x) may be 0.2, where a first spatial-void thickness is created followed by four additional spatial-void thickness simulated wellbores, each representing a 20% cement volumetric void space and five different locations throughout the annular thickness of the annulus 105. Therefore, the first spatial-void cement void position is 0, the second spatial-void cement position is 0.2, the third spatial-void cement position is 0.4, and so on until there are is no cement void space and thus n=1/(x) and has a value of 1. In yet other embodiments, (x) may represent any void thickness:cement thickness ratio for the first and at least one second spatial-void thickness simulated wellbores having gaps therein. In at least one embodiment, (x) for forming the first and at least second spatial-void thickness simulated wellbores is expressed as a decimal and is 0.1, 0.2, 0.3, 0.4, 0.5, 0.6, 0.7, 0.8, or 0.9.

Figure 9:
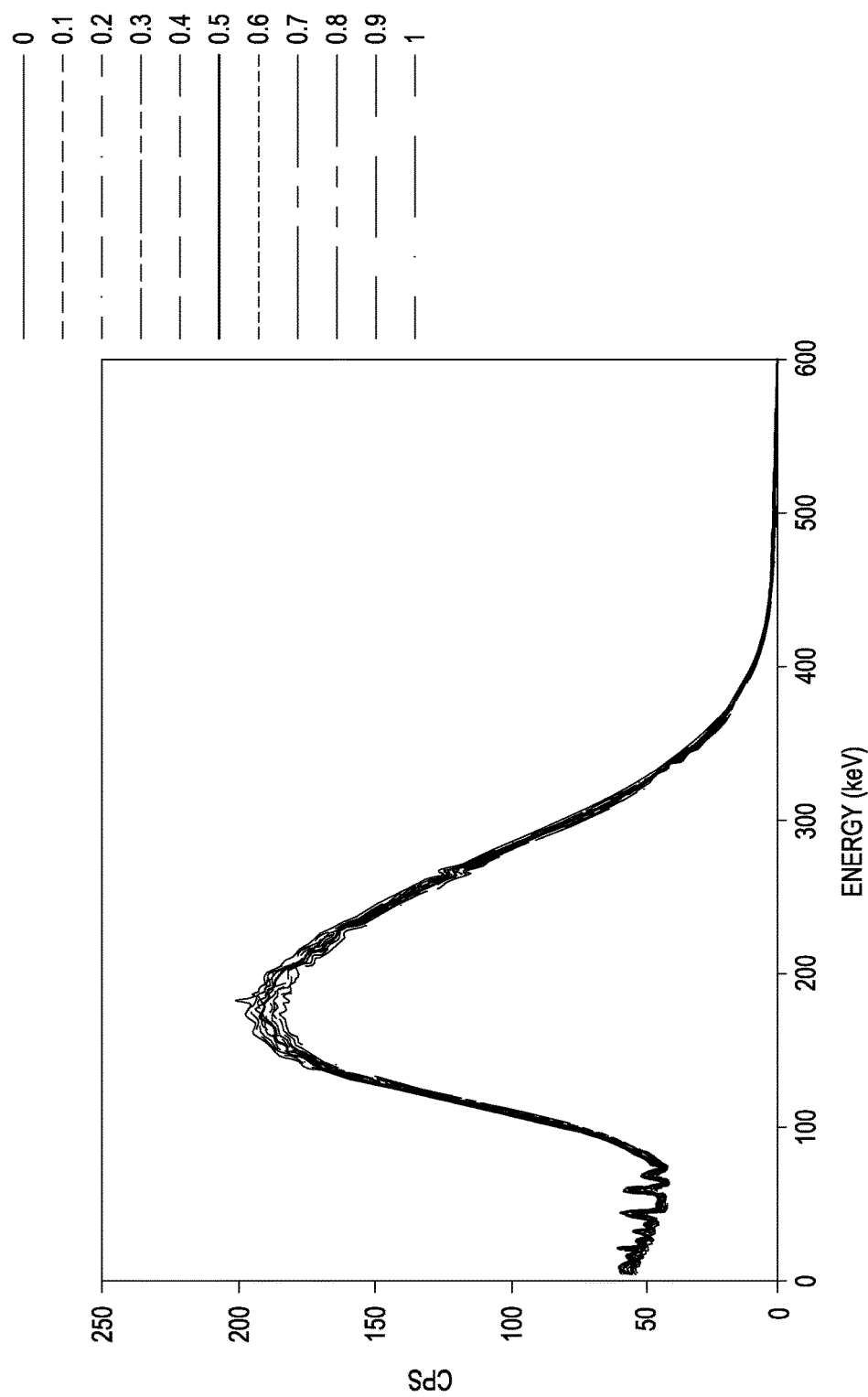
FIG. 9 is a graph showing detected gamma energy spectra for use in forming a cement-void-spatial calibration curve, according to one or more embodiments of the present disclosure.

Upon establishing the cement-only thickness simulated wellbore, the first spatial-void thickness simulated wellbore, and the at least one second spatial-void thickness simulated wellbore, a gamma spectrum is obtained for each simulated wellbore. Referring now to FIG. 9, illustrated is a graph depicting a series of gamma energy spectra obtained for use in forming the cement-void-spatial calibration curve described herein. The simulated wellbores used to establish the gamma spectra in FIG. 9 used water to simulate void space within an annulus having a particular completion profile, although any other non-cement void space fluid could also be used, without departing from the scope of the present disclosure. Accordingly, the "0" energy spectrum represents a first spatial-void thickness simulated wellbore, where the first spatial-void cement void position is adjacent to the casing string 102 and has a spatial resolution thickness of (x)=0.1. The "1" energy spectrum represents the cement-only thickness simulated wellbore having no cement 103 in the annulus 105. Therebetween are nine spectra representing 10% volumetric void space amounts at nine different cement void positions throughout the annular thickness of the annulus 105 (See, e.g., FIGS. 8A-8D).

Figure 10:
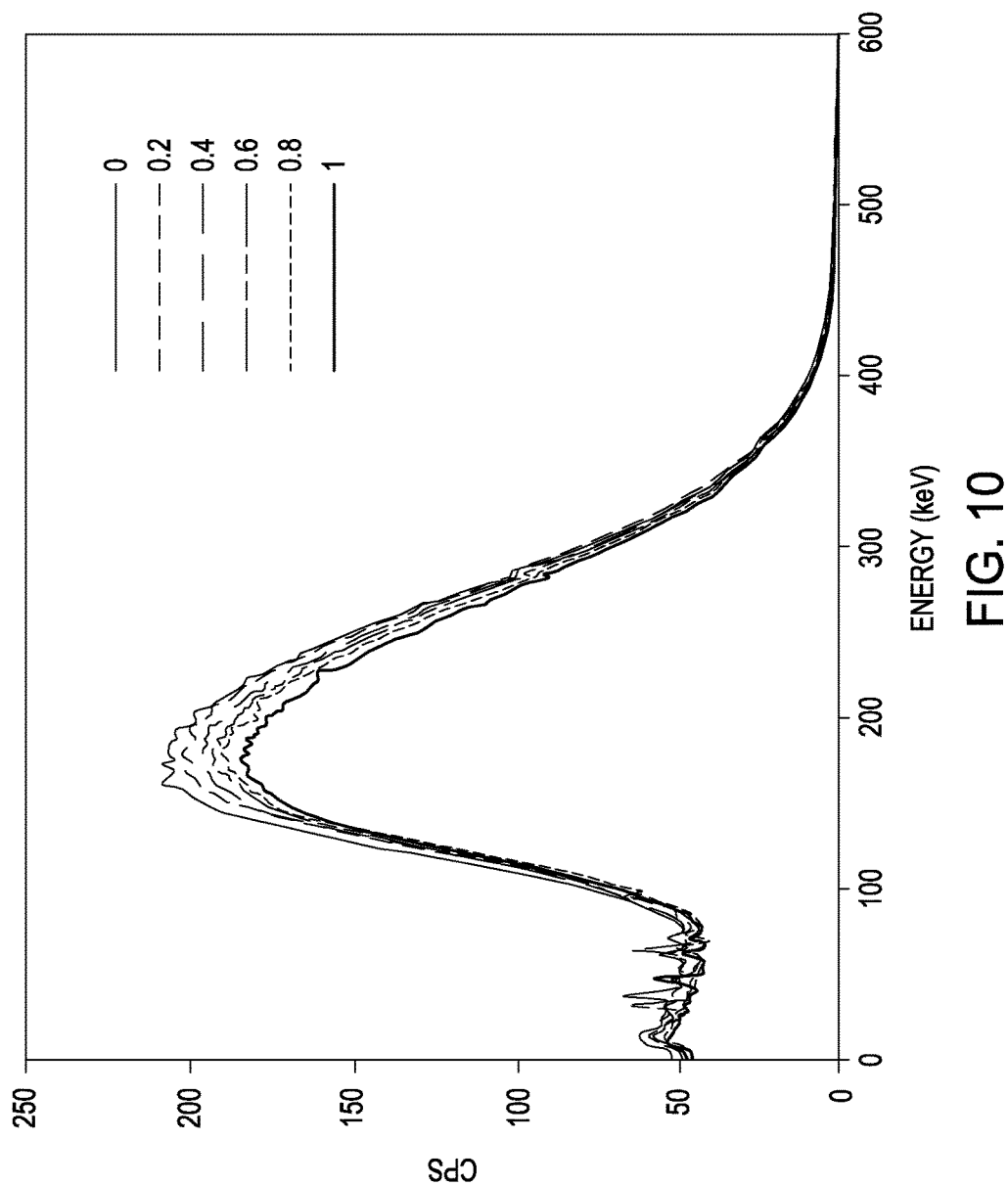
FIG. 10 is a graph showing detected gamma energy spectra for use in forming a cement-void-spatial calibration curve, according to one or more embodiments of the present disclosure.

Similarly, with reference to FIG. 10, illustrated is a graph depicting a series of gamma energy spectra obtained for use in forming the cement-void-spatial calibration curve described herein. The simulated wellbores used to establish the gamma spectra in FIG. 10 used water to simulate void space within an annulus having a particular completion profile, although any other non-cement void space fluid could also be used, without departing from the scope of the present disclosure. As described above, the "0" energy spectrum represents a first spatial-void thickness simulated wellbore, where the first spatial-void cement void position is adjacent to the casing string 102 and has a spatial resolution thickness of (x)=0.2. The "1" energy spectrum represents the cement-only thickness simulated wellbore having no cement 103 in the annulus 105. Therebetween are four spectra representing 20% volumetric void space amounts at four different locations throughout the annular thickness of the annulus 105 (See, e.g., FIGS. 8A-8D).

As shown in FIGS. 9 and 10, the defined energy range in which the simulated wellbores are evaluated is in the range of 0 keV to 600 keV. Accordingly, the defined energy range for forming the cement-void-spatial calibration curve may be in the range of about 0 keV to about 600 keV, encompassing any value and subset therebetween. In some embodiments, for example, the range may be a processing energy range (i.e., a more narrow energy range compared to the full energy range a gamma source can emit) of from about 150 keV to about 250 keV, encompassing any value and subset therebetween. As can be seen in FIGS. 9 and 10, the detected photon counts per second (CPS) are used to establish the cement-void-spatial calibration curve, as described in more detail below.

In some embodiments, the detected photon count rates for the obtained gamma spectra for the cement-only thickness simulated wellbore, the first spatial-void thickness simulated wellbore, and the at least second spatial-void thickness simulated wellbore are summed. Such summation may be within a defined processing gamma energy range, such as between about 150 keV and 250 keV, encompassing any value and subset therebetween. Accordingly, the detected photon count ranges for each of the various locations of the spatial resolution thickness (i.e., (x)) are summed for each gamma spectrum. Thereafter, the first and at least second spatial-void thickness summed photon count rates are normalized to the summed photon count rates of the cement-only thickness simulated wellbore gamma spectrum. The cement-void-spatial calibration curve is thus defined as the correspondence between the normalized summed photon count rates for the first spatial-void thickness simulated wellbore gamma spectrum and the at least second spatial-void thickness simulated wellbore, and the spatial resolution thickness (i.e., (x)).

Figure 11:
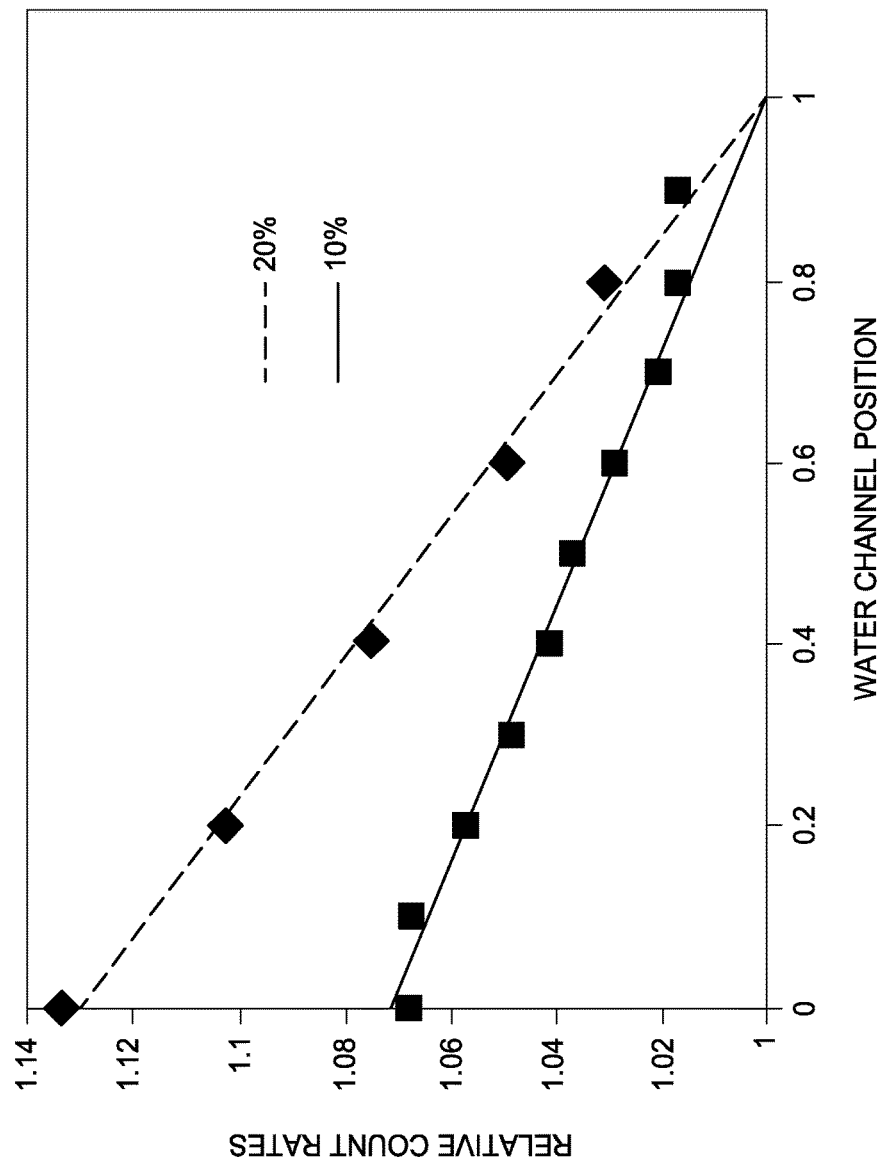
FIG. 11 is a graph of two cement-void-spatial calibration curves for two different cement volumetric void spaces having the same completion profile, according to one or more embodiments of the present disclosure.

Referring now to FIG. 11, illustrated is a graph of two cement-void-spatial calibration curves for two different cement volumetric void spaces having the same completion profile, according to one or more embodiments of the present disclosure. As shown in FIG. 11, the volumetric void space position is on the x-axis and normalized photon count rates are on the y-axis. As shown, a 20% and a 10% volumetric void space (equivalent to a spatial resolution thickness of (x)=0.2 and (x)=0.1, respectively) are shown, thus allowing a comparison of an obtained wellbore gamma spectrum to the cement-void-spatial calibration curve when the obtained wellbore gamma spectrum is taken from a wellbore having one or both of 20% or 10% volumetric void space at one or more target depths. The wellbore gamma spectrum, in this case, detected count rates, would be similarly normalized to allow comparison with the normalized photon count rates represented on the cement-void-spatial calibration curve.

Multiple cement-void-spatial calibration curves can be established based on different wellbore completion profiles and/or different spatial resolution amounts, without departing from the scope of the present disclosure. For example, a plurality of cement-void-spatial calibration curves may be established corresponding to a plurality of cement volumetric void space amounts in a wellbore at a plurality of depths.

The ability to determine both the cement volumetric void space amount and the location of such amount within an annulus permits an image of a void space distribution within a cement column at one or more locations to be realized. For example, a length, including the entire length or any portion thereof, or a single depth may be visually depicted. Such image or visual depiction may be manually realized or electronically realized by any means suitable for visualizing an image of the location and volume amount of void space in a cement column. In some embodiments, a user interface coupled to the control system described herein may be used to visually depict the cement void space amount and location within one or more target depths of a cement column.

Figure 12:
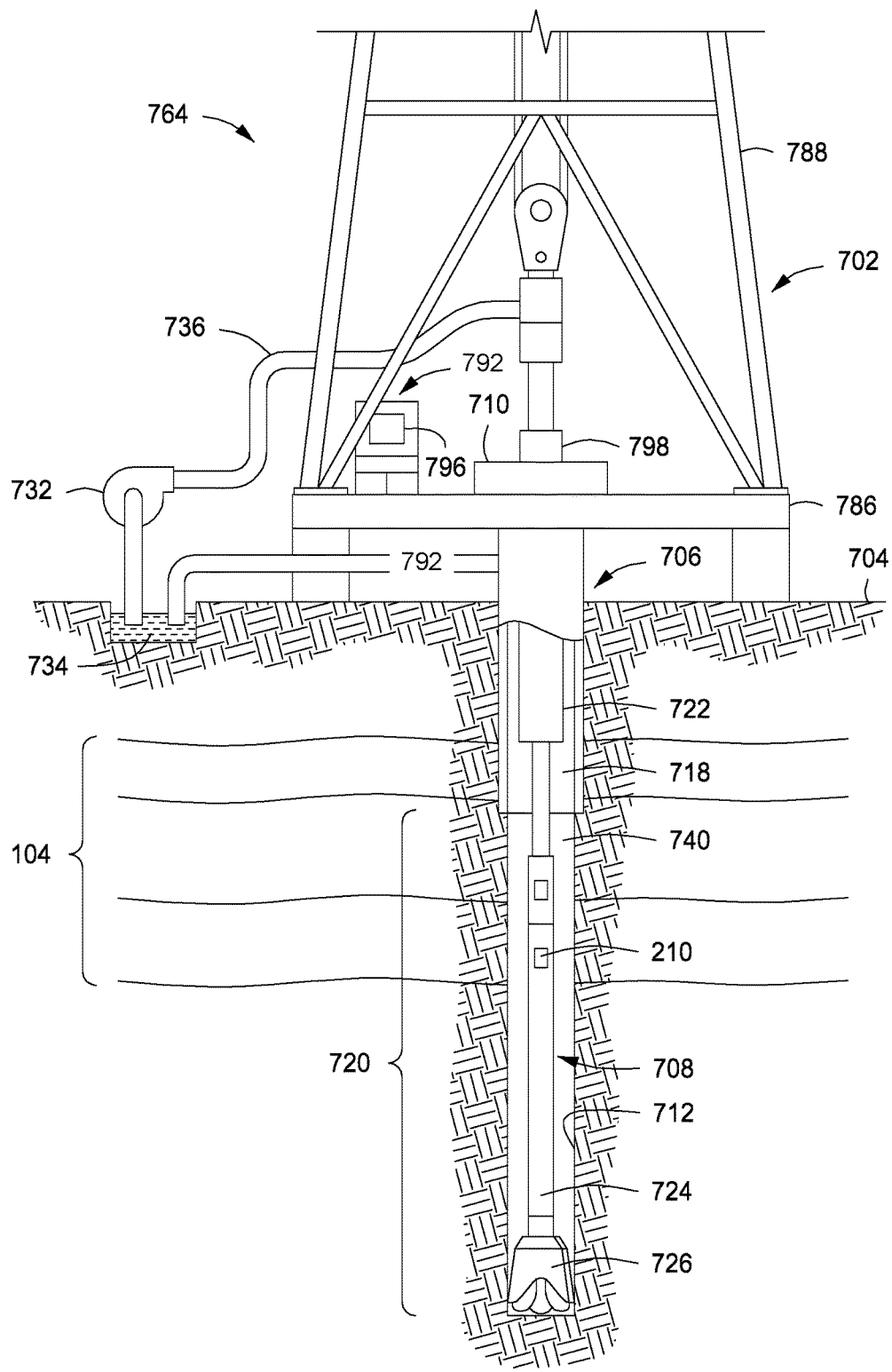
FIG. 12 is a diagram showing a drilling system, according to one or more embodiments of the present disclosure.

FIG. 12 is a diagram showing a drilling system 764, according to various embodiments of the present disclosure. The system 764 includes a drilling rig 702 located at the surface 704 of a well 706. The drilling rig 702 may provide support for a drillstring 708. The drillstring 708 may operate to penetrate the rotary table 710 for drilling the wellbore 712 through the subterranean formation 104. The drillstring 708 may include a drill pipe 718 and a bottom hole assembly (BHA) 720 (e.g., drill string), which may be located at the lower portion of the drill pipe 718.

The BHA 720 may include drill collars 722, a down hole tool 724 including the logging tool 210, and a drill bit 726. The drill bit 726 may operate to create the wellbore 712 by penetrating the surface 704 and the formation 104. The downhole tool 724 may comprise any of a number of different types of tools besides the logging tool 210, previously described. The logging tool 210 may be used in MWD/LWD operations within a wellbore 712 that has already been cased with casing and cement. Using the logging tool 210 during an MWD/LWD operation may provide data to the surface 704 (e.g., hardwired, telemetry) on already cased and cemented portions of the wellbore 712, even as other portions of the wellbore 712 are being drilled.

During drilling operations within the cased wellbore 712, the drillstring 708 (which may include the drill pipe 718 and the BHA 720) may be rotated by the rotary table 710. Although not shown, in addition to or alternatively, the BHA 720 may also be rotated by a motor (e.g., a mud motor) that is located below the surface 704. Drill collars 722 may be used to add weight to the drill bit 726. The drill collars 722 may also operate to stiffen the bottom hole assembly 720, allowing the bottom hole assembly 720 to transfer the added weight to the drill bit 726, and in turn, to assist the drill bit 726 in penetrating the surface 704 and the formation 104.

During drilling operations within the cased wellbore 712, a mud pump 732 may pump drilling fluid (which may also be referred to as "drilling mud") from a mud pit 734 through a hose 736 into the drill pipe 718 and down to the drill bit 726. The drilling fluid can flow out from the drill bit 726 and be returned to the surface 704 through an annular area 740 between the drill pipe 718 and the sides of the wellbore 712. The drilling fluid may then be returned to the mud pit 734, where such fluid is filtered, cleaned, or otherwise processed for reuse in the formation 104 (e.g., stimulation operations) or for resell for other industry use within and/or outside of the oil and gas industry. In some examples, the drilling fluid can be used to cool the drill bit 726, as well as to provide lubrication for the drill bit 726 during drilling operations. Additionally, the drilling fluid may be used to remove subsurface formation cuttings created by operating the drill bit 726.

A workstation 792 including a control system 796 may include various modules comprising a non-transitory medium (e.g., memory circuitry) readable for storing instructions for execution by a processor, and associated hardware circuitry, firmware, software, and combinations thereof configured to execute various embodiments described herein. For example, the control system may digitize gamma spectrum taken from the wellbore 712 using the logging tool 210, determine a cement volumetric void space in the wellbore (e.g., by computing a correlation coefficient between the digitized wellbore gamma spectrum and one or more digitized standard gamma so as to establish one or more wellbore HPFs at a target depth or location, comparing the wellbore HPF(s) to a digitized cement quality curve representing a volumetric void space of a completion profile matching that of the wellbore 712, and determining an output correlative to the volume of an unknown cement volumetric void space within an annulus of the wellbore 712), comparing the digitized wellbore gamma spectrum with a digitized cement-void-spatial calibration curved based on obtained gamma spectrum representing cement spatial void space locations corresponding to the cement volumetric void space amount, and determining a location of the cement volumetric void space in the wellbore.

As an example, the workstation 792 with control system 796 may be configured to digitize count rates of different gamma energy into multichannel spectra and generate formation 104-independent gamma energy spectra and use the spectra shape and amplitude to determine cement quality, according to the methods described previously. The control system 796 may be configured to store various cement quality curves of different completion profiles and instructions for determining wellbore HPF and quality curve HPF values, as well as to compare those values to determine cement quality (i.e., volumetric void space within a cement column). In some embodiments, the control system 796 may be configured to store various cement-void-spatial calibration curves of different completion profiles and different volumetric void space amounts, and instructions for determining a location of a known cement volumetric void space in a particular wellbore at one or more target locations. In some embodiments, the control system 796 may be configured to digitize the received one or more wellbore gamma spectrum and further determine a photon count rate, an amplitude, and a shape of the gamma spectra in order to determine the quality, volume, and/or location of the cement and voids therein based on the embodiments described herein.

Thus, in various examples, components of a system operable to conduct gamma energy photon digitization from the detector of the logging tool 210, as described herein or in a similar manner, which may be realized in combinations of hardware and/or processor executed software. These implementations can include a machine-readable storage device having machine-executable instructions, such as a computer-readable storage medium having computer-executable instructions. Further, a computer-readable storage medium may be a physical device that stores data represented by a physical structure within the device. Such a physical device is a non-transitory device. Examples of machine-readable storage devices may include, but are not limited to, read only memory (ROM), random access memory (RAM), a magnetic disk storage device, an optical storage device, a flash memory, other electronic, magnetic, and/or optical memory devices, and combinations thereof.

Figure 13:
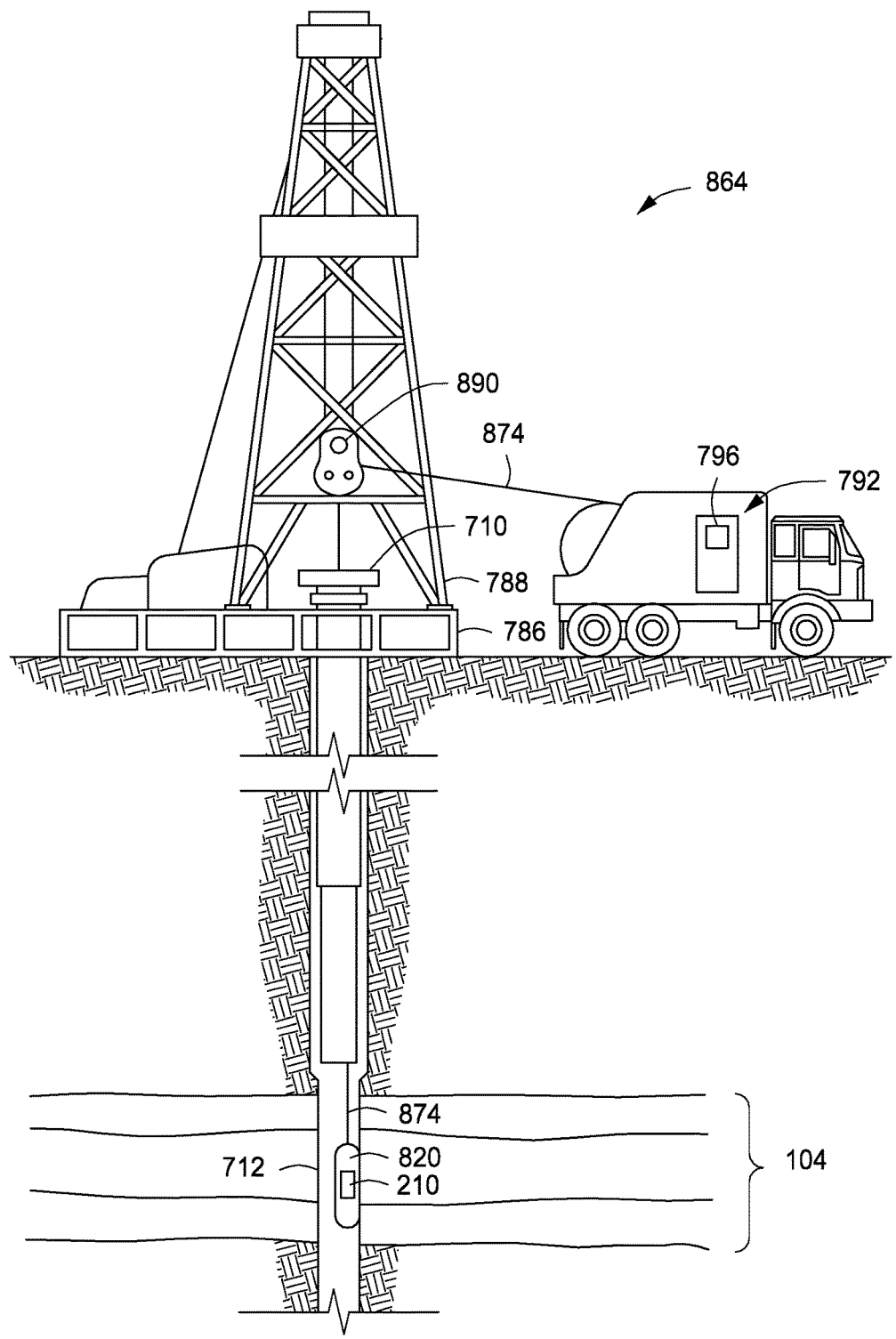
FIG. 13 is a diagram showing a wireline system, according to one or more embodiments of the present disclosure.

FIG. 13 is a diagram showing a wireline system 864, according to various examples of the disclosure. The system 864 may comprise a wireline logging tool body 820, as part of a wireline logging operation in a cased and cemented wellbore 712, which includes the logging tool 210 as described previously.

A drilling platform 786 equipped with a derrick 788 that supports a hoist 890 can be seen. Drilling oil and gas wells is commonly carried out using a string of drill pipes connected together so as to form a drillstring that is lowered through a rotary table 710 into the cased wellbore 712. As depicted, it is assumed that the drillstring has been temporarily removed from the wellbore 712 to allow the wireline logging tool body 820, such as a probe or sonde with the logging tool 210, to be lowered by wireline or logging cable 874 (e.g., a slickline cable) into the wellbore 712. Typically, the wireline logging tool body 820 is lowered to the region of interest (e.g., at a particular depth within the wellbore 712 or a particular location along the length of the wellbore, and subsequently pulled upward at typically a substantially constant speed. In an embodiment, the logging tool 210 is immediately adjacent to the wall of the wellbore 712, as previously discussed.

During the upward trip, at a series of depths, various instruments may be used to perform quality measurements on the cement column within the wellbore 712, including measurements taken by the logging tool 210, as described herein. Other types of measurements or measuring devices may be included in the wireline logging tool body 820, such as for measuring temperature, formation pressure, formation fluids, porosity, permeability, and the like, which may be taken in tandem or a different times and/or locations than the logging tool 210. The wireline data may be communicated to workstation 792 (i.e., a surface logging facility) for processing, analysis, visualization, and/or storage. The workstation 792 may be provided with electronic equipment for various types of signal processing as described previously. The workstation 792 may have a controller 796 that is coupled to the logging tool 210 through the wireline 874 or other telemetry in order to receive data from the logging tool 210 regarding the detected gamma photons and generate the energy spectra for use in determining wellbore HPF for use in determining a volumetric void space of cement and the location of the volumetric void space within an annulus between.

It should be noted that while FIGS. 12 and 13 generally depict a land-based systems, it is to be recognized that like systems may be operated in subsea locations as well. Moreover, it will be appreciated that although a vertical wellbore 712 is depicted in FIGS. 12 and 13, vertical or deviated wellbores, or combinations thereof, may additionally be used in accordance with the embodiments of the present disclosure. Additionally, the workstation 792 of FIG. 13 need not be located on a truck or be a mobile facility, as stationary facilities may also be used in accordance with the embodiments described herein.

Figure 14:
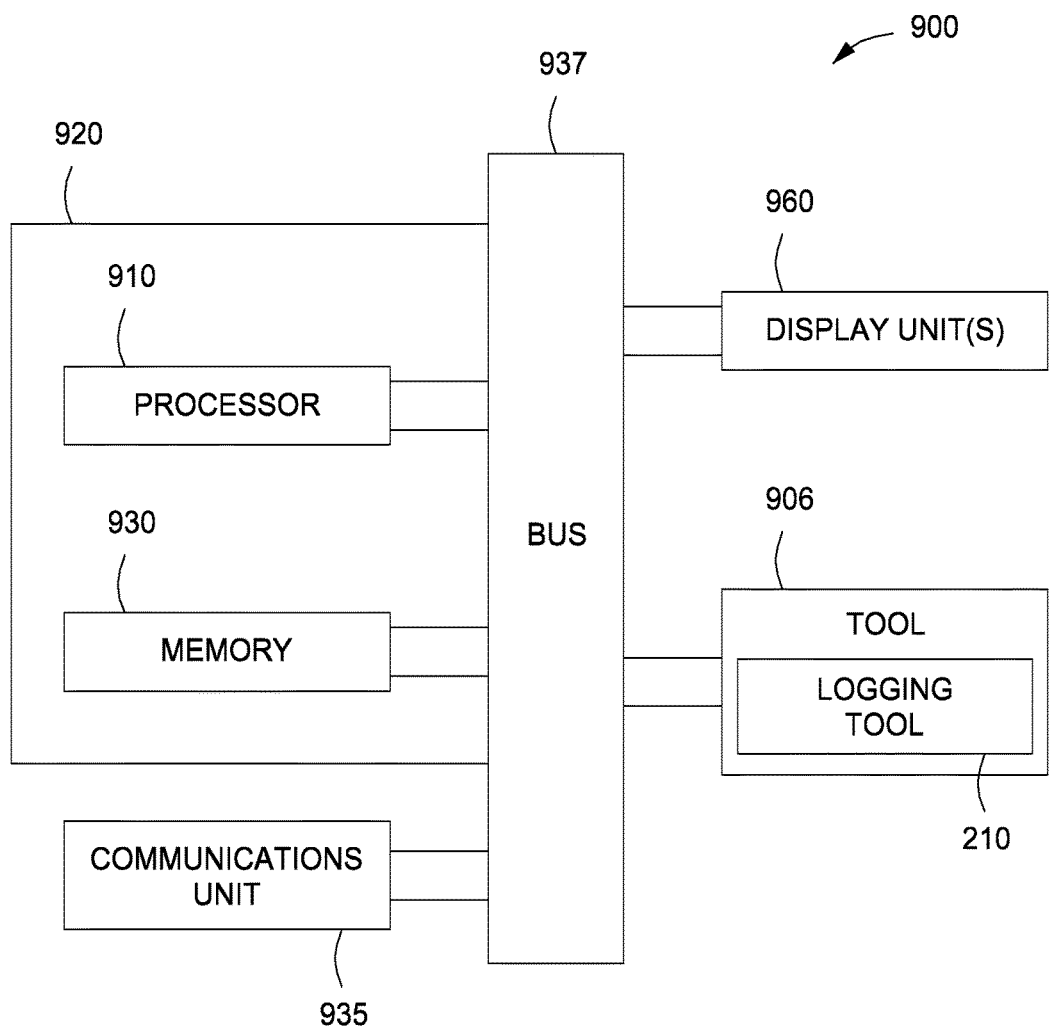
FIG. 14 is a block diagram of an example system operable to implement one or more embodiments of the present disclosure.

Referring now to FIG. 14, illustrated is a block diagram of an example system 900 operable to implement the activities of multiple methods, according to various embodiments of the present disclosure. The system 900 may include a tool housing 906 having the logging tool 210 such as that illustrated in FIG. 2. The system 900 may be configured to operate in accordance with the teachings herein to perform formation independent cement evaluation measurements in order to determine or utilize a known volumetric void space of cement in a cement column between a casing string and a formation to determine the location of said void space therein. The system 900 of FIG. 14 may be implemented as shown in FIGS. 12 and 13, with reference to the workstation 792 and control system 796.

The system 900 may include a control system 920 comprising memory 930 and a processor 910. The memory 930 may be structured to include a database. The system 900 may further include a communications unit 935. The processor 910 may be configured to digitize detected gamma photon count rates to generate multichannel gamma energy spectra having an amplitude and shape over a defined energy range that is a result of the change in cement volumetric void space and, thus, independent of the formation properties.

The communications unit 935 may include downhole communications for appropriately locating sensors in a wellbore. Such downhole communications may include, for example, a telemetry system. Such a system may allow a target depth to be reached for obtaining desired wellbore gamma spectra with the logging tool 210, as described herein. The communications unit 935 may use combinations of wired communication technologies and wireless technologies at frequencies that do not interfere with on-going measurements.

The system 900 may also include a bus 937, where the bus 937 provides electrical conductivity among the components of the system 900 (e.g., between the control system 920 and the detector of the logging tool 210). The bus 937 may include an address bus, a data bus, and a control bus, each independently configured or in an integrated format. The bus 937 may be realized using a number of different communication mediums that allow for the distribution of components of the system 900. The bus 937 may include a network. Use of the bus 937 may be regulated by the control system 920. The system 900 may include one or more display unit(s) 960 as a distributed component on the surface of a wellbore, which may be used with instructions stored in the memory 930 to implement a user interface to monitor the operation of the logging tool 210 or other components distributed within the system 900. The user interface may be used to input parameter values for thresholds such that the system 900 can operate substantially autonomously without user intervention in a variety of applications. The user interface may also provide for manual override and change of control of the system 900 to a user. Such a user interface may be operated in conjunction with the communications unit 935 and the bus 937. Furthermore, the user interface may be used to visually depict the location of one or more cement volumetric void spaces within the wellbore at one or more target depths, as previously mentioned, for imaging a full or one or more partial lengths of the cement column or a single target depth.

Embodiments disclosed herein include:

Embodiment A: A method comprising: taking a gamma spectrum from a wellbore at a target depth, wherein the wellbore penetrates a subterranean formation and has a completion profile comprising a pipe and an annulus between the pipe and the subterranean formation; determining a cement volumetric void space in the wellbore at the target depth; establishing a cement-void-spatial calibration curve based on obtained gamma spectra representing cement spatial void space locations in the annulus of the completion profile, wherein each cement volumetric void space amount in the wellbore has a characteristic cement-void-spatial calibration curve; comparing the wellbore gamma spectrum and the cement-void-spatial calibration curve; and determining a location of the cement volumetric void space in the wellbore at the target depth.

Embodiment A may have one or more of the following additional elements in any combination:

Element A1: Wherein the cement volumetric void space in the wellbore is determined based on a wellbore heterogeneity profiling factor (HPF) and a cement quality curve.

Element A2: Wherein the cement-void-spatial calibration curve is based on an electronically simulated wellbore or a physically simulated wellbore.

Element A3: Wherein the cement-void-spatial calibration curve is based on an electronically simulated wellbore using Monte Carlo simulation.

Element A4: Wherein the cement-void-spatial calibration curve is based on a detected photon count rate, an energy spectra shape, or an energy spectra amplitude in the wellbore gamma spectrum.

Element A5: Wherein the cement-void-spatial calibration curve is based on a normalized detected photon count rate, a normalized energy spectra shape, or a normalized energy spectra amplitude in the wellbore gamma spectrum.

Element A6: Wherein the cement-void-spatial calibration curve is established within a defined processing gamma energy range in the wellbore gamma spectrum.

Element A7: Wherein the cement-void-spatial calibration curve is established within a defined processing gamma energy range, and the defined processing gamma energy range is of from about 150 keV to about 250 keV within the wellbore gamma spectrum.

Element A8: Wherein the cement-void-spatial calibration curve is determined by: (a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness:cement thickness) in the annulus and corresponds to the cement volumetric void space amount in the wellbore; (b) establishing a cement-only thickness simulated wellbore having an assigned cement-only cement void position value of 1; (c) establishing a first spatial-void thickness simulated wellbore, wherein the first spatial-void thickness is adjacent to the pipe and equal to $(t)*(x)$, and has an assigned first spatial-void cement void position value of 0; (d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: $(t)*(n)*(x)$, where n represents an integer between 1 and $1/(x)$, and wherein the second spatial-void thickness simulated wellbore has a second spatial-void cement void position value of $(n)*(x)$; (e) obtaining a gamma spectrum for the cement-only thickness simulated wellbore, the first spatial-void thickness simulated wellbore, and the at least second spatial-void thickness simulated wellbore; (f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and (g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness.

Element A9: Wherein the cement-void-spatial calibration curve is determined by: (a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness:cement thickness) in the annulus and corresponds to the cement volumetric void space amount in the wellbore; (b) establishing a cement-only thickness simulated wellbore having an assigned cement-only cement void position value of 1; (c) establishing a first spatial-void thickness simulated wellbore, wherein the first spatial-void thickness is adjacent to the pipe and equal to $(t)*(x)$, and has an assigned first spatial-void cement void position value of 0; (d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: $(t)*(n)*(x)$, where n represents an integer between 1 and $1/(x)$, and wherein the second spatial-void thickness simulated wellbore has a second spatial-void cement void position value of $(n)*(x)$; (e) obtaining a gamma spectrum for the cement-only thickness simulated wellbore, the first spatial-void thickness simulated wellbore, and the at least second spatial-void thickness simulated wellbore; (f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and (g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness, wherein (x) in steps (d) and (e) is expressed as a decimal and is 0.1, 0.2, 0.3, 0.4, 0.5, 0.6, 0.7, 0.8, or 0.9.

Element A10: Wherein a plurality of cement-void-spatial calibration curves are established corresponding to a plurality of cement volumetric void space amounts in the wellbore at a plurality of target depths.

Element A11: Wherein a plurality of cement-void-spatial calibration curves are established corresponding to a plurality of cement volumetric void space amounts in the wellbore at a plurality of target depths, and further comprising generating a visual depiction of the location of the cement volumetric void space at the plurality of target depths.

By way of non-limiting example, exemplary combinations applicable to A include: A1-A11; A2, A4, and A9; A1, A3, A6, and A8; A4 and A11; A5, A6, and A7; A8 and A10; A2, A5, A7, and A9; and the like.

Embodiment B: A system comprising: a conveyance extending into a wellbore penetrating a subterranean formation, wherein the wellbore has a completion profile comprising a pipe and an annulus between the pipe and the subterranean formation; a downhole logging tool coupled to the conveyance, the downhole logging tool comprising a gamma source and a detector for obtaining a gamma spectrum of the wellbore at a target depth; and a control system coupled to the detector, the control system comprising a non-transitory medium readable for storing instructions for execution by a processor for performing a method, the method comprising: digitizing the gamma spectrum of the wellbore at the target depth; determining a cement volumetric void space in the wellbore at the target depth; comparing the digitized wellbore gamma spectrum with a digitized cement-void-spatial calibration curve based on obtained gamma spectra representing cement spatial void space locations in the annulus of the completion profile, wherein each cement volumetric void space amount has a characteristic digitized cement-void-spatial calibration curve; and determining a location of the cement volumetric void space in the wellbore at the target depth.

Embodiment B may have one or more of the following additional elements in any combination:

Element B1: Wherein cement volumetric void space in the wellbore is determined based on a wellbore heterogeneity profiling factor (HPF) and a cement quality curve.

Element B2: Wherein the digitized cement-void-spatial calibration curve is based on an electronically simulated wellbore or a physically simulated wellbore.

Element B3: Wherein the digitized cement-void-spatial calibration curve is based on an electronically simulated wellbore using Monte Carlo simulation.

Element B4: Wherein the digitized cement-void-spatial calibration curve is based on a detected photon count rate, an energy spectra shape, or an energy spectra amplitude in the digitized wellbore gamma spectrum.

Element B5: Wherein the digitized cement-void-spatial calibration curve is established within a defined processing gamma energy range in the digitized wellbore gamma spectrum.

Element B6: Wherein the digitized cement-void-spatial calibration curve is determined by: (a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness:cement thickness) in the annulus and corresponds to the cement volumetric void space amount in the wellbore; (b) establishing a cement-only thickness simulated wellbore having an assigned cement-only cement void position value of 1; (c) establishing a first spatial-void thickness simulated wellbore, wherein the first spatial-void thickness is adjacent to the pipe and equal to $(t)*(x)$, and has an assigned first spatial-void cement void position value of 0; (d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: $(t)*(n)*(x)$, where n represents an integer between 1 and $1/(x)$, and wherein the second spatial-void thickness simulated wellbore has a second spatial-void cement void position value of $(n)*(x)$; (e) obtaining a gamma spectrum for the cement-only thickness simulated wellbore, the first spatial-void thickness simulated wellbore, and the at least second spatial-void thickness simulated wellbore; (f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and (g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness.

Element B7: Wherein the digitized cement-void-spatial calibration curve is determined by: (a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness:cement thickness) in the annulus and corresponds to the cement volumetric void space amount in the wellbore; (b) establishing a cement-only thickness simulated wellbore having an assigned cement-only cement void position value of 1; (c) establishing a first spatial-void thickness simulated wellbore, wherein the first spatial-void thickness is adjacent to the pipe and equal to $(t)*(x)$, and has an assigned first spatial-void cement void position value of 0; (d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: $(t)*(n)*(x)$, where n represents an integer between 1 and $1/(x)$, and wherein the second spatial-void thickness simulated wellbore has a second spatial-void cement void position value of $(n)*(x)$; (e) obtaining a gamma spectrum for the cement-only thickness simulated wellbore, the first spatial-void thickness simulated wellbore, and the at least second spatial-void thickness simulated wellbore; (f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and (g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness, and wherein (x) in steps (d) and (e) is expressed as a decimal and is 0.1, 0.2, 0.3, 0.4, 0.5, 0.6, 0.7, 0.8, or 0.9.

Element B8: Further comprising a user interface for visually depicting the location of the cement volumetric void space in the wellbore at the target depth.

By way of non-limiting example, exemplary combinations applicable to B include: B1-B8; B2, B4, B6, and B7; B1 and B9; B5 and B8; B4, B6, B8, and B9; B1 and B2; B1, B4, and B7; and the like.

Therefore, the embodiments disclosed herein are well adapted to attain the ends and advantages mentioned as well as those that are inherent therein. The particular embodiments disclosed above are illustrative only, as they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A method comprising:
    taking a gamma spectrum from a wellbore at a target depth, wherein the wellbore penetrates a subterranean formation and has a completion profile comprising a pipe and an annulus between the pipe and the subterranean formation, wherein there is a cement column disposed within the annulus;
    determining a quantitative amount of cement volumetric void space in the cement column at the target depth;
    establishing a cement-void-spatial calibration curve based on obtained gamma spectra representing one or more locations of the cement spatial void spaces in the annulus of the completion profile, wherein the quantitative amount of each cement volumetric void space in the wellbore has a characteristic cement-void-spatial calibration curve;
    comparing the wellbore gamma spectrum and the cement-void-spatial calibration curve; and
    determining a distance of the one or more locations of the cement volumetric void spaces within the cement column from an inner surface and outer surface of the cement column at the target depth.

2. The method of claim 1, wherein the amount of cement volumetric void space in the cement column is determined based on a wellbore heterogeneity profiling factor (HPF) and a cement quality curve.

3. The method of claim 1, wherein the cement-void-spatial calibration curve is based on an electronically simulated wellbore or a physically simulated wellbore.

4. The method of claim 1, wherein the cement-void-spatial calibration curve is based on an electronically simulated wellbore using Monte Carlo simulation.

5. The method of claim 1, wherein the cement-void-spatial calibration curve is based on a detected photon count rate, an energy spectra shape, or an energy spectra amplitude in the wellbore gamma spectrum.

6. The method of claim 1, wherein the cement-void-spatial calibration curve is based on a normalized detected photon count rate, a normalized energy spectra shape, or a normalized energy spectra amplitude in the wellbore gamma spectrum.

7. The method of claim 1, wherein the cement-void-spatial calibration curve is established within a defined processing gamma energy range in the wellbore gamma spectrum.

8. The method of claim 1, wherein the cement-void-spatial calibration curve is established within a defined processing gamma energy range, and the defined processing gamma energy range is of from about 150 keV to about 250 keV within the wellbore gamma spectrum.

9. The method of claim 1, wherein the cement-void-spatial calibration curve is determined by:
    (a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness: cement thickness) in the annulus and corresponds to the amount of the cement volumetric void space in the wellbore;
    (b) establishing a cement-only thickness simulated wellbore having an assigned cement-only cement void position value of 1;
    (c) establishing a first spatial-void thickness simulated wellbore, wherein the first spatial-void thickness is adjacent to the pipe and equal to (t)*(x), and has an assigned first spatial-void cement void position value of 0;
    (d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: (t)*(n)*(x), where n represents an integer between 1 and 1/(x), and wherein the second spatial-void thickness simulated wellbore has a second spatial-void cement void position value of (n)*(x);
    (e) obtaining a gamma spectrum for the cement-only thickness simulated wellbore, the first spatial-void thickness simulated wellbore, and the at least second spatial-void thickness simulated wellbore;
    (f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and (g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness.

10. The method of claim 9, wherein (x) in steps (d) and (e) is expressed as a decimal and is 0.1, 0.2, 0.3, 0.4, 0.5, 0.6, 0.7, 0.8, or 0.9.

11. The method of claim 1, wherein a plurality of cement-void-spatial calibration curves are established corresponding to a plurality of cement volumetric void spaces in the cement column at a plurality of target depths.

12. The method of claim 1, wherein a plurality of cement-void-spatial calibration curves are established corresponding to a plurality of cement volumetric void spaces in the cement column at a plurality of target depths, and further comprising generating a visual depiction of the location of the cement volumetric void spaces at the plurality of target depths.

13. A system comprising:
a conveyance extending into a wellbore penetrating a subterranean formation, wherein the wellbore has a completion profile comprising a pipe and an annulus between the pipe and the subterranean formation, wherein there is a cement column disposed within the annulus;
a downhole logging tool coupled to the conveyance, the downhole logging tool comprising a gamma source and a detector for obtaining a gamma spectrum of the wellbore at a target depth; and
a control system coupled to the detector, the control system comprising a non-transitory medium readable for storing instructions for execution by a processor configured to:
digitize the gamma spectrum of the wellbore at the target depth;
determining a quantitative amount of cement volumetric void space in the wellbore at the target depth;
compare the digitized wellbore gamma spectrum with a digitized cement-void-spatial calibration curve based on obtained gamma spectra representing the one or more locations of the cement spatial void spaces in the annulus of the completion profile, wherein each cement volumetric void space has a characteristic digitized cement-void-spatial calibration curve; and
determining a distance of one or more locations of the cement volumetric void spaces within the cement column from an inner surface and outer surface of the cement column at the target depth.

14. The system of claim 13, wherein amount of cement volumetric void space in the wellbore is determined based on a wellbore heterogeneity profiling factor (HPF) and a cement quality curve.

15. The system of claim 13, wherein the digitized cement-void-spatial calibration curve is based on an electronically simulated wellbore or a physically simulated wellbore.

16. The system of claim 13, wherein the digitized cement-void-spatial calibration curve is based on an electronically simulated wellbore using Monte Carlo simulation.

17. The system of claim 13, wherein the digitized cement-void-spatial calibration curve is based on a detected photon count rate, an energy spectra shape, or an energy spectra amplitude in the digitized wellbore gamma spectrum.

18. The system of claim 13, wherein the digitized cement-void-spatial calibration curve is established within a defined processing gamma energy range in the digitized wellbore gamma spectrum.

19. The system of claim 13, wherein the digitized cement-void-spatial calibration curve is determined by:
(a) creating a plurality of simulated wellbores having the completion profile comprising the annulus between the pipe and the subterranean formation, where (t) is the thickness of the annulus, and (x) is a spatial resolution thickness defined as a ratio of void thickness to cement thickness (void thickness: cement thickness) in the annulus and corresponds to the amount of the cement volumetric void space in the wellbore;
(b) establishing a cement-only thickness simulated wellbore having an assigned cement-only cement void position value of 1;
(c) establishing a first spatial-void thickness simulated wellbore, wherein the first spatial-void thickness is adjacent to the pipe and equal to (t)*(x), and has an assigned first spatial-void cement void position value of 0;
(d) establishing at least a second spatial-void thickness simulated wellbore, wherein the at least second spatial-void thickness is adjacent to the first spatial-void thickness and toward the subterranean formation, wherein a spacing between the second spatial-void thickness and the pipe is defined according to the Formula: (t)*(n)*(x), where n represents an integer between 1 and 1/(x), and wherein the second spatial-void thickness simulated wellbore has a second spatial-void cement void position value of (n)*(x);
(e) obtaining a gamma spectrum for the cement-only thickness simulated wellbore, the first spatial-void thickness simulated wellbore, and the at least second spatial-void thickness simulated wellbore;
(f) summing photon count rates for each of the cement-only thickness simulated wellbore gamma spectrum, the first spatial-void thickness simulated wellbore gamma spectrum, and the at least second spatial-void thickness simulated wellbore gamma spectrum, wherein the summed photon count rates are each within an identically defined processing gamma energy range; and
(g) normalizing the summed photon count rates for the first spatial-void thickness simulated wellbore gamma spectrum and the at least second spatial-void thickness simulated wellbore gamma spectrum to the summed photon count rates of the cement-only thickness simulated wellbore gamma spectrum, wherein the correspondence between the normalized summed photon count rates for the first spatial-void thickness simulated wellbore gamma spectrum and the at least second spatial-void thickness simulated wellbore gamma spectrum, and a position of the first spatial-void thickness and the at least second spatial-void thickness defines the cement-void-spatial calibration curve for the spatial resolution thickness.

20. The system of claim 13, further comprising a user interface for visually depicting the location of the cement volumetric void space in the wellbore at the target depth.

* * * * *